(12) United States Patent
Verard et al.

(10) Patent No.: US 8,046,052 B2
(45) Date of Patent: *Oct. 25, 2011

(54) NAVIGATION SYSTEM FOR CARDIAC THERAPIES

(75) Inventors: Laurent Verard, Andover, MA (US); Mark W. Hunter, Broomfield, CO (US); Andrew Bzostek, Erie, CO (US)

(73) Assignee: Medtronic Navigation, Inc., Louisville, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 12/730,714

(22) Filed: Mar. 24, 2010

(65) Prior Publication Data

US 2010/0210938 A1  Aug. 19, 2010

Related U.S. Application Data

(63) Continuation of application No. 10/619,216, filed on Jul. 14, 2003, now Pat. No. 7,697,972, which is a continuation-in-part of application No. 10/299,969, filed on Nov. 19, 2002, now Pat. No. 7,599,730.

(51) Int. Cl.
*A61B 5/05* (2006.01)
(52) U.S. Cl. .......................... 600/424; 600/407; 600/428
(58) Field of Classification Search .................. 600/407, 600/424, 428, 433, 437
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bronhardt | |
| 2,407,845 A | 9/1946 | Nemeyer | |
| 2,650,588 A | 9/1953 | Drew | |
| 2,697,433 A | 12/1954 | Sehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,294,083 A | 12/1966 | Alderson | |
| 3,367,326 A | 2/1968 | Frazier | |
| 3,439,256 A | 4/1969 | Kahne | |
| 3,577,160 A | 5/1971 | White | |

(Continued)

FOREIGN PATENT DOCUMENTS

CA  964149 A1  3/1975

(Continued)

OTHER PUBLICATIONS

"Prestige Cervical Disc System Surgical Technique", 12 pgs.

(Continued)

*Primary Examiner* — Michael T Rozanski
(74) *Attorney, Agent, or Firm* — Harness, Dickey

(57) ABSTRACT

An image guided navigation system for navigating a region of a patient includes an imaging device, a tracking device, a controller, and a display. The imaging device generates images of the region of a patient. The tracking device tracks the location of the instrument in a region of the patient. The controller superimposes an icon representative of the instrument onto the images generated from the imaging device based upon the location of the instrument. The display displays the image with the superimposed instrument. The images and a registration process may be synchronized to a physiological event. The controller may also provide and automatically identify an optimized site to navigate the instrument to.

22 Claims, 16 Drawing Sheets

U.S. PATENT DOCUMENTS

| | | |
|---|---|---|
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |

| Patent No. | Date | Inventor |
|---|---|---|
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |

| | | | | | |
|---|---|---|---|---|---|
| 5,596,228 A | 1/1997 | Anderton et al. | 5,803,089 A | 9/1998 | Ferre et al. |
| 5,600,330 A | 2/1997 | Blood | 5,807,252 A | 9/1998 | Hassfeld et al. |
| 5,603,318 A | 2/1997 | Heilbrun et al. | 5,810,008 A | 9/1998 | Dekel et al. |
| 5,611,025 A | 3/1997 | Lorensen et al. | 5,810,728 A | 9/1998 | Kuhn |
| 5,617,462 A | 4/1997 | Spratt | 5,810,735 A | 9/1998 | Halperin et al. |
| 5,617,857 A | 4/1997 | Chader et al. | 5,820,553 A | 10/1998 | Hughes |
| 5,619,261 A | 4/1997 | Anderton | 5,823,192 A | 10/1998 | Kalend et al. |
| 5,622,169 A | 4/1997 | Golden et al. | 5,823,958 A | 10/1998 | Truppe |
| 5,622,170 A | 4/1997 | Schulz | 5,828,725 A | 10/1998 | Levinson |
| 5,627,873 A | 5/1997 | Hanover et al. | 5,828,770 A | 10/1998 | Leis et al. |
| 5,628,315 A | 5/1997 | Vilsmeier et al. | 5,829,444 A | 11/1998 | Ferre et al. |
| 5,630,431 A | 5/1997 | Taylor | 5,831,260 A | 11/1998 | Hansen |
| 5,636,644 A | 6/1997 | Hart et al. | 5,833,608 A | 11/1998 | Acker |
| 5,638,819 A | 6/1997 | Manwaring et al. | 5,834,759 A | 11/1998 | Glossop |
| 5,640,170 A | 6/1997 | Anderson | 5,836,954 A | 11/1998 | Heilbrun et al. |
| 5,642,395 A | 6/1997 | Anderton et al. | 5,840,024 A | 11/1998 | Taniguchi et al. |
| 5,643,268 A | 7/1997 | Vilsmeier et al. | 5,840,025 A | 11/1998 | Ben-Haim |
| 5,645,065 A | 7/1997 | Shapiro et al. | 5,843,076 A | 12/1998 | Webster, Jr. et al. |
| 5,646,524 A | 7/1997 | Gilboa | 5,848,967 A | 12/1998 | Cosman |
| 5,647,361 A | 7/1997 | Damadian | 5,851,183 A | 12/1998 | Bucholz |
| 5,662,111 A | 9/1997 | Cosman | 5,865,846 A | 2/1999 | Bryan et al. |
| 5,664,001 A | 9/1997 | Tachibana et al. | 5,868,674 A | 2/1999 | Glowinski et al. |
| 5,674,296 A | 10/1997 | Bryan et al. | 5,868,675 A | 2/1999 | Henrion et al. |
| 5,676,673 A | 10/1997 | Ferre et al. | 5,871,445 A | 2/1999 | Bucholz |
| 5,681,260 A | 10/1997 | Ueda et al. | 5,871,455 A | 2/1999 | Ueno |
| 5,682,886 A | 11/1997 | Delp et al. | 5,871,487 A | 2/1999 | Warner et al. |
| 5,682,890 A | 11/1997 | Kormos et al. | 5,873,822 A | 2/1999 | Ferre et al. |
| 5,690,108 A | 11/1997 | Chakeres | 5,882,304 A | 3/1999 | Ehnholm et al. |
| 5,694,945 A | 12/1997 | Ben-Haim | 5,884,410 A | 3/1999 | Prinz |
| 5,695,500 A | 12/1997 | Taylor et al. | 5,889,834 A | 3/1999 | Vilsmeier et al. |
| 5,695,501 A | 12/1997 | Carol et al. | 5,891,034 A | 4/1999 | Bucholz |
| 5,696,500 A | 12/1997 | Diem | 5,891,157 A | 4/1999 | Day et al. |
| 5,697,377 A | 12/1997 | Wittkampf | 5,904,691 A | 5/1999 | Barnett et al. |
| 5,702,406 A | 12/1997 | Vilsmeier | 5,907,395 A | 5/1999 | Schulz et al. |
| 5,711,299 A | 1/1998 | Manwaring et al. | 5,913,820 A | 6/1999 | Bladen et al. |
| 5,713,946 A | 2/1998 | Ben-Haim | 5,920,395 A | 7/1999 | Schulz |
| 5,715,822 A | 2/1998 | Watkins et al. | 5,921,992 A | 7/1999 | Costales et al. |
| 5,715,836 A | 2/1998 | Kliegis et al. | 5,923,727 A | 7/1999 | Navab |
| 5,718,241 A | 2/1998 | Ben-Haim et al. | 5,928,248 A | 7/1999 | Acker |
| 5,727,552 A | 3/1998 | Ryan | 5,935,160 A | 8/1999 | Auricchio et al. |
| 5,727,553 A | 3/1998 | Saad | 5,938,603 A | 8/1999 | Ponzi |
| 5,729,129 A | 3/1998 | Acker | 5,938,694 A | 8/1999 | Jaraczewski et al. |
| 5,730,129 A | 3/1998 | Darrow et al. | 5,947,980 A | 9/1999 | Jensen et al. |
| 5,730,130 A | 3/1998 | Fitzpatrick et al. | 5,947,981 A | 9/1999 | Cosman |
| 5,732,703 A | 3/1998 | Kalfas et al. | 5,950,629 A | 9/1999 | Taylor et al. |
| 5,735,278 A | 4/1998 | Hoult et al. | 5,951,475 A | 9/1999 | Gueziec et al. |
| 5,738,096 A | 4/1998 | Ben-Haim | 5,951,571 A | 9/1999 | Audette |
| 5,740,802 A | 4/1998 | Nafis et al. | 5,954,647 A | 9/1999 | Bova et al. |
| 5,740,808 A | 4/1998 | Panescu et al. | 5,954,796 A | 9/1999 | McCarty et al. |
| 5,741,214 A | 4/1998 | Ouchi et al. | 5,957,844 A | 9/1999 | Dekel et al. |
| 5,742,394 A | 4/1998 | Hansen | 5,964,796 A | 10/1999 | Imran |
| 5,744,953 A | 4/1998 | Hansen | 5,967,980 A | 10/1999 | Ferre et al. |
| 5,748,767 A | 5/1998 | Raab | 5,967,982 A | 10/1999 | Barnett |
| 5,749,362 A | 5/1998 | Funda et al. | 5,968,047 A | 10/1999 | Reed |
| 5,749,835 A | 5/1998 | Glantz | 5,971,997 A | 10/1999 | Guthrie et al. |
| 5,752,513 A | 5/1998 | Acker et al. | 5,976,156 A | 11/1999 | Taylor et al. |
| 5,755,725 A | 5/1998 | Druais | 5,980,535 A | 11/1999 | Barnett et al. |
| RE35,816 E | 6/1998 | Schulz | 5,983,126 A | 11/1999 | Wittkampf |
| 5,758,667 A | 6/1998 | Slettenmark | 5,987,349 A | 11/1999 | Schulz |
| 5,762,064 A | 6/1998 | Polvani | 5,987,960 A | 11/1999 | Messner et al. |
| 5,767,669 A | 6/1998 | Hansen et al. | 5,999,837 A | 12/1999 | Messner et al. |
| 5,767,699 A | 6/1998 | Bosnyak et al. | 5,999,840 A | 12/1999 | Grimson et al. |
| 5,767,960 A | 6/1998 | Orman | 6,001,130 A | 12/1999 | Bryan et al. |
| 5,769,789 A | 6/1998 | Wang et al. | 6,004,269 A | 12/1999 | Crowley et al. |
| 5,769,843 A | 6/1998 | Abela et al. | 6,006,126 A | 12/1999 | Cosman |
| 5,769,861 A | 6/1998 | Vilsmeier | 6,006,127 A | 12/1999 | Van Der Brug et al. |
| 5,772,594 A | 6/1998 | Barrick | 6,013,087 A | 1/2000 | Adams et al. |
| 5,775,322 A | 7/1998 | Silverstein et al. | 6,014,580 A | 1/2000 | Blume et al. |
| 5,776,064 A | 7/1998 | Kalfas et al. | 6,016,439 A | 1/2000 | Acker |
| 5,782,765 A | 7/1998 | Jonkman | 6,019,725 A | 2/2000 | Vesely et al. |
| 5,787,886 A | 8/1998 | Kelly et al. | 6,024,695 A | 2/2000 | Taylor et al. |
| 5,792,055 A | 8/1998 | McKinnon | 6,050,724 A | 4/2000 | Schmitz et al. |
| 5,795,294 A | 8/1998 | Luber et al. | 6,059,718 A | 5/2000 | Taniguchi et al. |
| 5,797,849 A | 8/1998 | Vesely et al. | 6,063,022 A | 5/2000 | Ben-Haim |
| 5,799,055 A | 8/1998 | Peshkin et al. | 6,071,288 A | 6/2000 | Carol et al. |
| 5,799,099 A | 8/1998 | Wang et al. | 6,073,043 A | 6/2000 | Schneider |
| 5,800,352 A | 9/1998 | Ferre et al. | 6,076,008 A | 6/2000 | Bucholz |
| 5,800,535 A | 9/1998 | Howard, III | 6,096,050 A | 8/2000 | Audette |
| 5,802,719 A | 9/1998 | O'Farrell, Jr. et al. | 6,104,944 A | 8/2000 | Martinelli |

| | | |
|---|---|---|
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,207,111 B1 | 3/2001 | Weinberg |
| 6,210,362 B1 | 4/2001 | Ponzi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,379,302 B1 | 4/2002 | Kessman et al. |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,504 B1 | 9/2002 | Ben-Haim et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,493,575 B1 | 12/2002 | Kesten et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,574,498 B1 | 6/2003 | Gilboa |
| 6,584,174 B2 | 6/2003 | Schubert et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,725,080 B2 | 4/2004 | Melkent et al. |
| 6,892,090 B2 | 5/2005 | Verard et al. |
| 6,950,689 B1 | 9/2005 | Willis et al. |
| 7,130,700 B2 | 10/2006 | Gardeski et al. |
| 7,570,791 B2 | 8/2009 | Frank et al. |
| 7,599,730 B2 | 10/2009 | Hunter et al. |
| 7,697,972 B2 | 4/2010 | Verard et al. |
| 2001/0007918 A1 | 7/2001 | Vilsmeier et al. |
| 2001/0036245 A1 | 11/2001 | Kienzle et al. |
| 2002/0077568 A1 | 6/2002 | Haddock |
| 2002/0095081 A1 | 7/2002 | Vilsmeier et al. |
| 2002/0128565 A1 | 9/2002 | Rudy |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0078494 A1 | 4/2003 | Panescu et al. |
| 2004/0024309 A1 | 2/2004 | Ferre et al. |
| 2004/0097805 A1 | 5/2004 | Verard et al. |
| 2004/0097806 A1 | 5/2004 | Hunter et al. |
| 2005/0143651 A1 | 6/2005 | Verard et al. |
| 2007/0049817 A1 | 3/2007 | Preiss et al. |
| 2009/0262992 A1 | 10/2009 | Markowitz et al. |
| 2009/0264752 A1 | 10/2009 | Markowitz et al. |
| 2009/0281417 A1 | 11/2009 | Hartmann et al. |
| 2010/0022873 A1 | 1/2010 | Hunter et al. |
| 2010/0030061 A1 * | 2/2010 | Canfield et al. ............... 600/413 |
| 2010/0030063 A1 | 2/2010 | Lee et al. |
| 2010/0152571 A1 | 6/2010 | Hartmann et al. |

FOREIGN PATENT DOCUMENTS

| | | |
|---|---|---|
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1393674 A1 | 3/2004 |
| EP | 1421913 A1 | 5/2004 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1983 |
| JP | 63240851 A | 10/1988 |
| JP | 2765738 T | 4/1991 |
| JP | 3267054 | 11/1991 |
| JP | 6194639 | 7/1994 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |

| | | | |
|---|---|---|---|
| WO | WO-9838908 A1 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0006701 A1 | 2/2000 |
| WO | WO-0035531 A1 | 6/2000 |
| WO | WO-0130437 A1 | 5/2001 |
| WO | WO-0187136 A2 | 11/2001 |
| WO | WO-02064011 A2 | 8/2002 |
| WO | WO-2008147961 A1 | 12/2008 |

OTHER PUBLICATIONS

"Vital Images Receives 510(k) Clearance to Market VScore(TM) With AutoGate(TM); Breakthrough in Cardiac CT Imaging Simplifies Screening for Heart Disease," Press Release. Vital Images, Inc., Feb. 6, 2001 (4 pages).

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

European Search Report completed Mar. 1, 2004 for European application EP03024327, claiming benefit of U.S. Appl. No. 10/299,969, filed Nov. 19, 2002.

European Search Report completed Sep. 29, 2004 for European application EP04016056, claiming benefit of U.S. Appl. No. 10/619,216, filed Jul. 14, 2003.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The SteathStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164 (May 1, 1994) pp. 137-145.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13 (1994) pp. 193-211.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Intracardiac Echocardiographic Guidance & Monitoring During Percutaneous Endomyocardial Gene Injection in Porcine Heart, Seung, et al. (Human Gene Therapy 12:893-903 May 20, 2001).

Jacob, Al, et al., "A Whole-Body Registration-Free Navigation System for Image-Guided Surgery and Interventional Radiology," Investigative Radiology, vol. 35 No. 5 (May 2000) pp. 279-288.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and lmgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51 (1996) pp. 635-638.

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. Car '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble. (1995).

Lavallee et al., "Image guided operating robot: a clinical application in stereotactic neurosurgery," Proceedings of the 1992 IEEE International Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11.sup.th Annual International Conference, 1989, pp. 0926-0927.

Lavallee, "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Cotonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96.

Muschlitz, Lin, "Ultrasound in the OR suite is providing more detailed information to allow less invasive surgeries." Technology—Ultra Sound Surgical Partners (Sep. 2003) Medical Imaging. http://www.imagingeconomics.com/issues/articles/MI_2003-09_03.asp (accessed on Aug. 12, 2010).

Ng, W.S. et al., Robotic Surgery—A First-Hand Experience in Transurethral Resection of the Prostate Surgery, IEEE Eng. in Med. and Biology, pp. 120-125 (Mar. 1993).

Partial European Search Report completed Mar. 1, 2004 for European application EP03024327, claiming benefit of U.S. Appl. No. 10/299,969, filed Nov. 19, 2002.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12.sup.th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Enffernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery (1996) pp. 329-341.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS (1995) pp. 185-192.

Smith et al., "Computer Methods for Improved Diagnostic Image Display Applied to Stereotactic Neurosurgery," Automedical, vol. 14, 1992, pp. 371-382.

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al.; Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," (1997) pp. 119-128.

Invitation to Pay Additional Fees mailed Mar. 5, 2010 for PCT/US2009/067486 claiming benefit of U.S. Appl. No. 12/336,085, filed Dec. 16, 2008.

International Search Report and Written Opinion mailed May 4, 2010 for PCT/US2009/067486 claiming benefit of U.S. Appl. No. 12/336,085, filed Dec. 16, 2008.

* cited by examiner

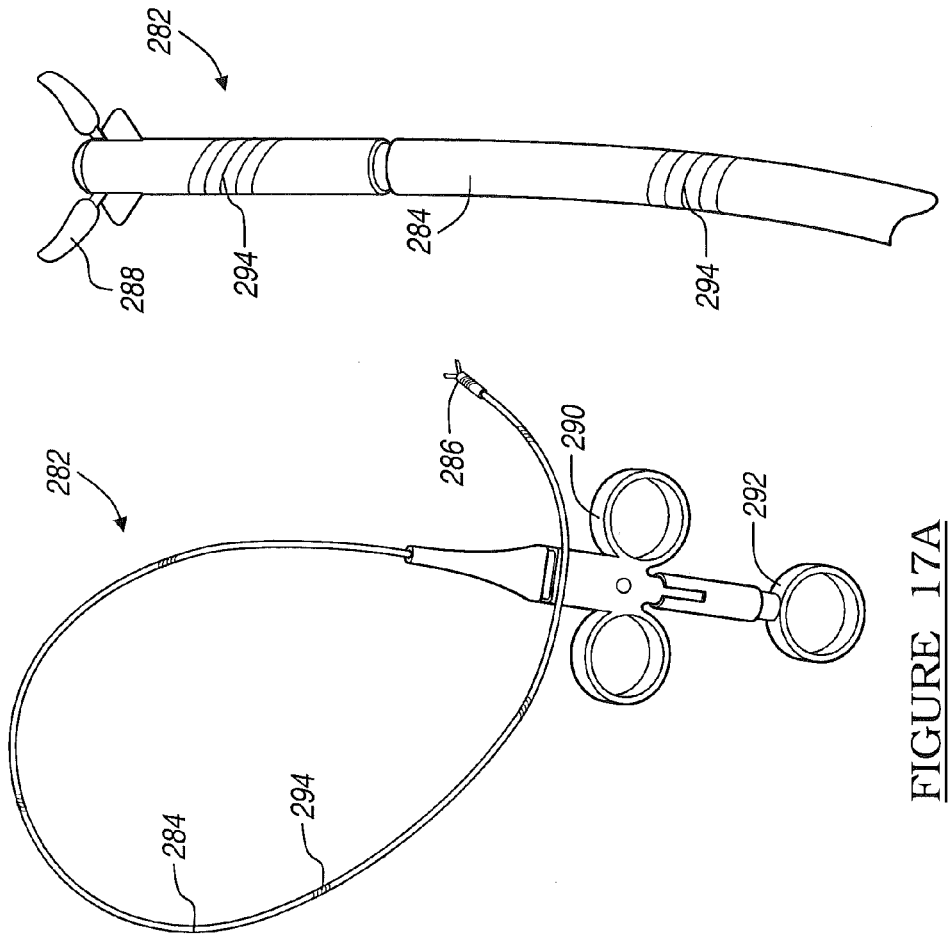
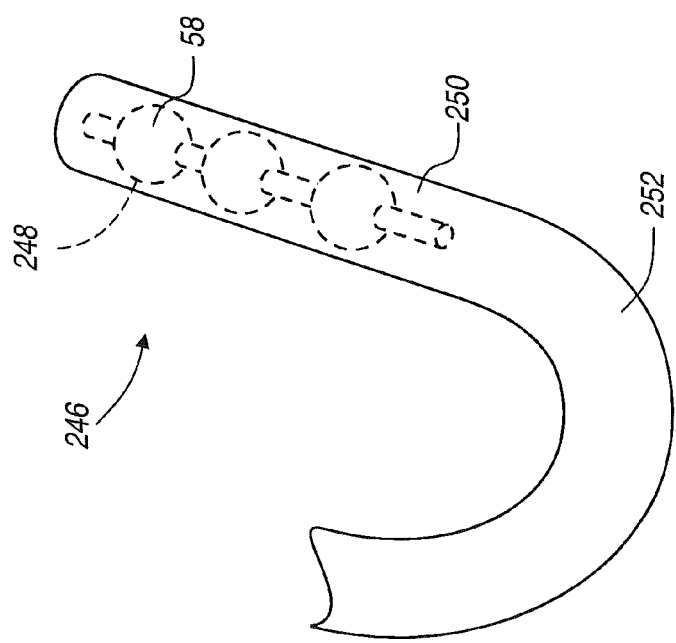
FIGURE 17B
FIGURE 17A
FIGURE 16

NAVIGATION SYSTEM FOR CARDIAC THERAPIES

CROSS-REFERENCE TO RELATED APPLICATIONS

This application is a continuation of U.S. patent application Ser. No. 10/619,216 filed on Jul. 14, 2003, now U.S. Pat. No. 7,697,972, issued Apr. 13, 2010, which is a continuation-in-part of U.S. patent application Ser. No. 10/299,969 filed on Nov. 19, 2002, now U.S. Pat. No. 7,599,730, issued Oct. 6, 2009, which is hereby incorporated by reference.

FIELD OF THE INVENTION

The present invention relates generally to image guided surgery, and more specifically, to systems and methods for using one or more medical images to assist in navigating an instrument through internal body structures, in particular for navigating a catheter in a moving body structure, such as the heart, during a surgical procedure.

BACKGROUND OF THE INVENTION

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), isocentric C-arm fluoroscopic imaging, positron emission tomography (PET), and ultrasound imaging (US) has increased the interest in image guided medical procedures.

At present, cardiac catheterization procedures are typically performed with the aid of fluoroscopic images. Two-dimensional fluoroscopic images taken intra-procedurally allow a physician to visualize the location of a catheter being advanced through cardiovascular structures. However, use of such fluoroscopic imaging throughout a procedure exposes both the patient and the operating room staff to radiation, as well as exposes the patient to contrast agents. Therefore, the number of fluoroscopic images taken during a procedure is preferably limited to reduce the radiation exposure to the patient and staff.

An image guided surgical navigation system that enables the physician to see the location of an instrument relative to a patient's anatomy, without the need to acquire real-time fluoroscopic images throughout the surgical procedure is generally disclosed in U.S. Pat. No. 6,470,207, entitled "Navigational Guidance Via Computer-Assisted Fluoroscopic Imaging," issued Oct. 22, 2002, which is incorporated herein by reference in its entirety. In this system, representations of surgical instruments are overlaid on pre-acquired fluoroscopic images of a patient based on the position of the instruments determined by a tracking sensor.

Other types of procedures include the use of electro physiologic mapping catheters to map the heart based on measured electrical potentials. Such mapping catheters are useful in identifying an area of tissue that is either conducting normally or abnormally, however, some mapping catheters may not aid in actually guiding a medical device to a targeted tissue area for medical treatment.

Other procedures that could benefit from a navigation system include cardiac lead placement. Cardiac lead placement is important in achieving proper stimulation or accurate sensing at a desired cardiac location. Endocardial is one type of lead placement procedure that is an internal procedure where coronary vein leads are generally implanted with the use of a guide catheter and/or a guide wire or stylet to achieve proper placement of the lead. Epicardial is another type of procedure that is an external procedure for cardiac lead placement that may also benefit from this navigation system. A coronary vein lead may be placed using a multi-step procedure wherein a guide catheter is advanced into the coronary sinus ostium and a guide wire is advanced further through the coronary sinus and great cardiac vein to a desired cardiac vein branch. Because the tip of a guide wire is generally flexible and may be preshaped in a bend or curve, the tip of the guide wire can be steered into a desired venous branch. The guide wire tip is directed with a steerable guide catheter, and with the appropriate pressure, it is manipulated into the desired vein branch.

A cardiac lead may therefore be advanced to a desired implant location using a guide wire extending entirely through the lead and out its distal end. Cardiac leads generally need to be highly flexible in order to withstand flexing motion caused by the beating heart without fracturing. A stiff stylet or guide wire provides a flexible lead with the stiffness needed to advance it through a venous pathway. Leads placed with the use of a stylet or guide wire are sometimes referred to as "over-the-wire" leads. Once the lead is placed in a desired location, the guide wire and guide catheter may be removed. A guide wire placed implantable lead is disclosed in U.S. Pat. No. 6,192,280, entitled "Guidewire Placed Implantable Lead With Tip Seal," issued Feb. 20, 2001. A coronary vein lead having a flexible tip and which may be adapted for receiving a stylet or guide wire is disclosed in U.S. Pat. No. 5,935,160, entitled "Left ventricular access lead for heart failure pacing", issued Aug. 10, 1999, each of which are hereby incorporated by reference.

Also, pacing lead procedures currently performed today for use in heart failure treatment are not optimized. In this regard, the lead placement is not optimized due to the lack of having real-time anatomic information, navigation and localization information, hemo-dynamic data, and electrophysiological data. Thus, pacing leads are currently simply "stuffed" into the heart without any optimization being performed due to lack of information that can be used for this optimization.

Advancement of a guide catheter or an over-the-wire lead through a vessel pathway and through cardiac structures requires considerable skill and can be a time-consuming task. This type of procedure also exposes the patient to an undesirable amount of radiation exposure and contrast agent. Therefore, it is desirable to provide an image guided navigation system that allows the location of a guide catheter being advanced within the cardiovascular structures for lead placement to be followed in either two, three, or four dimensional space in real time. It is also desirable to provide an image guided navigation system that assists in navigating an instrument, such as a catheter, through a moving body structure or any type of soft tissue.

With regard to navigating an instrument through a moving body structure, difficulties arise in attempting to track such an instrument using known tracking technology as the instrument passes adjacent or through a moving body structure, since the virtual representation of the instrument may be offset from the corresponding anatomy when superimposed onto image data. Accordingly, it is also desirable to acquire image data and track the instrument in a synchronized manner with the pre-acquired image using gating or synchronization techniques, such as ECG gating or respiratory gating.

Other difficulties with cardiac procedures include annual check-ups to measure early indications for organ rejection in heart transplant patients. These indicators include white blood cells, chemical change, blood oxygen levels, etc. During the procedure, an endovascular biopsy catheter is inserted into the heart and multiple biopsies are performed in the septum wall of the heart. Again, during this procedure, radiation and contrast agent is utilized to visualize the biopsy catheter, thereby exposing both a patient and the doctor to potential excess radiation and contrast agents during the procedure. As such, it would also be desirable to provide an image guided navigation system that assists in performing this type of procedure in order to reduce radiation and contrast agent exposure.

Other types of surgical procedures also suffer from certain disadvantages. For example, with neurological diseases, these diseases are generally treated and accessed from the cranium down to the neurological site in order to reach tumors, ventricles, or treat different ailments, such as Parkinson's disease. This type of invasive procedure creates significant trauma, such as skull holes, dura opening, fiber destruction, and other cerebral structural damage or leakage. It is, therefore, also desirable to provide a minimally invasive approach to treat such ailments, which are accessible from either vascular or the cerebrospinal fluid tree.

Other types of vascular techniques includes use of a device referred to as an intravascular ultrasound (IVUS) technique. This type of technique is typically used to visualize tissue and/or blood vessels within the patient. This technique involves the use of a disposable catheter that includes an ultrasound transducer positioned within the catheter in order to provide two-dimensional ultrasound images as the catheter is passed through a vessel. However, this type of vascular technique has various drawbacks. For example, this type of disposable IVUS catheter is extremely expensive. Moreover, the ultrasound transducer embedded within the catheter provides only visualization on one side of the catheter, typically orthogonal to the catheter body, and therefore does not provide any forward views or other views about the catheter. Thus, here again, it is also desirable to provide an improved intravascular ultrasound approach, which substantially reduces the cost and increases the field of view of existing technologies. Still further, it is also desirable to register ultrasound image information with other or multiple image modalities, which are each registered to one another and viewed on a single or multiple displays.

SUMMARY OF THE INVENTION

A navigation system is provided including a catheter carrying single or multiple localization sensors, a sensor interface, a user interface, a controller, and a visual display. Aspects of the present invention allow for the location of a catheter advanced within an internal space within the human body, for example within the cardiovascular structures, to be identified in two, three or four dimensions in real time. Further aspects of the present invention allow for accurate mapping of a tissue or organ, such as the heart or other soft tissue, and/or precise identification of a desired location for delivering a medical lead or other medical device or therapy while reducing the exposure to fluoroscopy normally required during conventional catheterization procedures. These types of therapies include, but are not limited to, drug delivery therapy, cell delivery therapy, ablation, stenting, or sensing of various physiological parameters with the appropriate type of sensor. In cardiac applications, methods included in the present invention compensate for the effects of respiration and the beating heart that can normally complicate mapping or diagnostic data. Aspects of the present invention may be tailored to improve the outcomes of numerous cardiac therapies as well as non-cardiac therapies, such as neurological, oncological, or other medical therapies, including lung, liver, prostate and other soft tissue therapies, requiring the use of a catheter or other instrument at a precise location.

The steerable catheter provided by the present invention features at least one or more, location sensors located near the distal end of an elongated catheter body. The location sensors may be spaced axially from each other and may be electromagnetic detectors. An electromagnetic source is positioned externally to the patient for inducing a magnetic field, which causes voltage to be developed on the location sensors. The location sensors may be each electrically coupled to twisted pair conductors, which extend through the catheter body to the proximal catheter end. Twisted pair conductors provide electromagnetic shielding of the conductors, which prevents voltage induction along the conductors when exposed to the magnetic flux produced by the electromagnetic source. Alternatively, the sensors and the source may be reversed where the catheter emits a magnetic field that is sensed by external sensors.

By sensing and processing the voltage signals from each location sensor, the location of the catheter tip with respect to the external sources and the location of each sensor with respect to one another may be determined. The present invention allows a two, three, or four-dimensional reconstruction of several centimeters of the distal portion of the catheter body in real time. Visualization of the shape and position of a distal portion of the catheter makes the advancement of the catheter to a desired position more intuitive to the user. The system may also provide a curve fitting algorithm that is selectable based upon the type of catheter used, and based upon the flexibility of the catheter, based upon a path finding algorithm, and based upon image data. This enables estimated curved trajectories of the catheter to be displayed to assist the user.

In an alternative embodiment, the location sensors may be other types of sensors, such as conductive localization sensors, accelerometer localized sensors, fiberoptic localization sensors, or any other type of location sensor.

The catheter body is formed of a biocompatible polymer having stiffness properties that allow torsional or linear force applied to a handle at the proximal end to be transferred to the distal end in such a way that the catheter may be advanced in a desired direction. The catheter body includes multiple lumens for carrying conductors to sensors located at or near the distal end of the catheter and a guide wire extending from a proximal handle to the distal catheter tip. The guide wire aids in steering the catheter through a venous pathway, or other body lumens, and can be manipulated at its proximal end to cause bending or curving of the distal catheter tip.

In addition to the location sensors, the catheter may be equipped with one or more sensors for providing useful clinical data related to the catheter position or for identifying a target tissue site at which a medical device or medical therapy will be delivered. Additional sensors may include electrodes for sensing depolarization signals occurring in excitable tissue such as the heart, nerve or brain. In one embodiment, for use in cardiac applications, at least one electrode may be provided at or near the distal end of the catheter for sensing internal cardiac electrogram (EGM) signals. In other embodiments, an absolute pressure sensor may be provided on the catheter body near the distal end to monitor blood pressure. In still other embodiments, the catheter may be equipped with other sensors of physiological signals such as oxygen saturation or motion sensors.

The catheter body further provides a lumen through which a medical device or medical therapy may be delivered. For example, a medical lead for cardiac pacing or cardioversion or defibrillation may be introduced through a lumen of the catheter body. Alternatively, pharmaceutical agents, ablation catheters, cell therapies, genetic therapies, or other medical devices or therapies may be delivered through a lumen of the catheter body after it has been located at a targeted tissue site. The system may also provide a map identifying the delivery of the therapy, which can be annotated on 2D, 3D or 4D images or provided as a graphic representation of the cell or drug delivery. These distribution maps show how the drug, cell or other therapies are distributed on the heart or other soft tissue. The catheter may also be used to deliver energy for ablation, deliver hot/cold or thermal cutting apparatuses, deliver mechanical forces to provide therapy or deliver water jets to provide other means of cutting.

The location sensor conductors, as well as conductors coupled to other physiological sensors present, are coupled to a sensor interface for filtering, amplifying, and digitizing the sensed signals. The digitized signals are provided via a data bus to a control system, embodied as a computer. Programs executed by the control system process the sensor data for determining the location of the location sensors relative to a reference source. A determined location is superimposed on a two, three, or four-dimensional image that is displayed on a monitor. A user-interface, such as a keyboard, mouse or pointer, is provided for entering operational commands or parameters.

In one embodiment, a sensed EGM signal and/or an absolute pressure signal may be used in conjunction with location sensor data to establish and verify the location of the distal end of the catheter as it is advanced through the cardiovascular system. Characteristic EGM or pressure signals that are known to occur at different locations in the heart allow for location reference points to be recognized for further verification of the catheter location. The catheter may then be maneuvered through the cardiovascular structures with the location of the distal portion of the catheter superimposed on the heart model display as an icon or other soft tissue models.

In one embodiment, the catheter may also be provided with an automatic catheter-steering mechanism. Thermal shape-memory metal film may be incorporated in the distal portion of the catheter body. Selected heating of the metal film causes bending or curving of the catheter so that it may automatically be steered to a desired location.

In another embodiment, an image guided navigation system for guiding an instrument through a region of the patient includes an anatomic gating device, an imaging device, a tracking device, a controller and a display. The anatomic gating device senses a physiological event. The imaging device captures image data in response to the physiological event. The tracking device tracks the position of the instrument in the region of the patient. The controller is on communication with the anatomic gating device, the imaging device and the tracking device and registers the image data with the region of a patient in response to the physiological event. The controller also superimposes an icon representing the instrument onto the image data, based on the tracked position. The display displays the image data of the region of the patient with the superimposed icon of the instrument.

In another embodiment, an image guided navigation system for navigating to an optimized site in the patient using image data includes an instrument, a tracking device, at least one sensor, a controller and a display. The instrument is navigated to the optimized site. The tracking device is attached to the instrument and is used to track the position of the instrument in the patient. The sensor is attached to the instrument and senses a physiological parameter in the patient. The controller tracks the position of the instrument with the tracking device and receives the sensed physiological parameter from the sensor. The controller also estimates the optimized site and superimposes an icon representing the location of the optimized site and an icon representing the instrument, based on the sensed physiological parameter and the position of the instrument. The display displays the icon of the estimated optimized site and the icon representing the instrument in the patient.

In yet another embodiment, an image guided navigation system for navigating a region of a patient includes an imaging device, an instrument, a first tracking device, a controller and a display. The imaging device is positioned outside the patient and generates image data at the region of the patient. The instrument is navigated in the region of the patient. The first tracking device is attached to the instrument and is used to track the position of the instrument in the region of the patient. The controller generates virtual images along the navigated path of the instrument from the image data generated outside the patient. The display displays the virtual images.

In still another embodiment, a method for image guiding the instrument in a region of a patient includes identifying a physiological event, capturing image data during the physiological event, registering the captured image data to the patient during the physiological event, and displaying the location of the instrument on the image data by superimposing an icon of the instrument on the image data.

In still another embodiment, the method for image guiding an instrument to an optimized site includes navigating the instrument in the patient, detecting a location of the instrument, sensing a physiological parameter with the instrument, automatically determining an optimized site to navigate the instrument to and displaying an icon of the optimized site and an icon of the location of the catheter.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 16 is another embodiment of a catheter employed in cardiac therapies, according to the teachings of the present invention;

FIGS. 17a and 17b illustrate a navigable biopsy instrument, according to the teachings of the present invention;

DETAILED DESCRIPTION OF THE PREFERRED EMBODIMENTS

The following description of the preferred embodiment(s) is merely exemplary in nature and is in no way intended to limit the invention, its application, or uses. As indicated above, the present invention is directed at providing improved, non-line-of-site image-guided navigation of an instrument, such as a catheter, balloon catheter, implant, lead, stent, needle, guide wire, insert and/or capsule, that may be used for physiological monitoring, delivering a medical therapy, or guiding the delivery of a medical device in an internal body space, such as the heart or any other region of the body.

Figure 1:
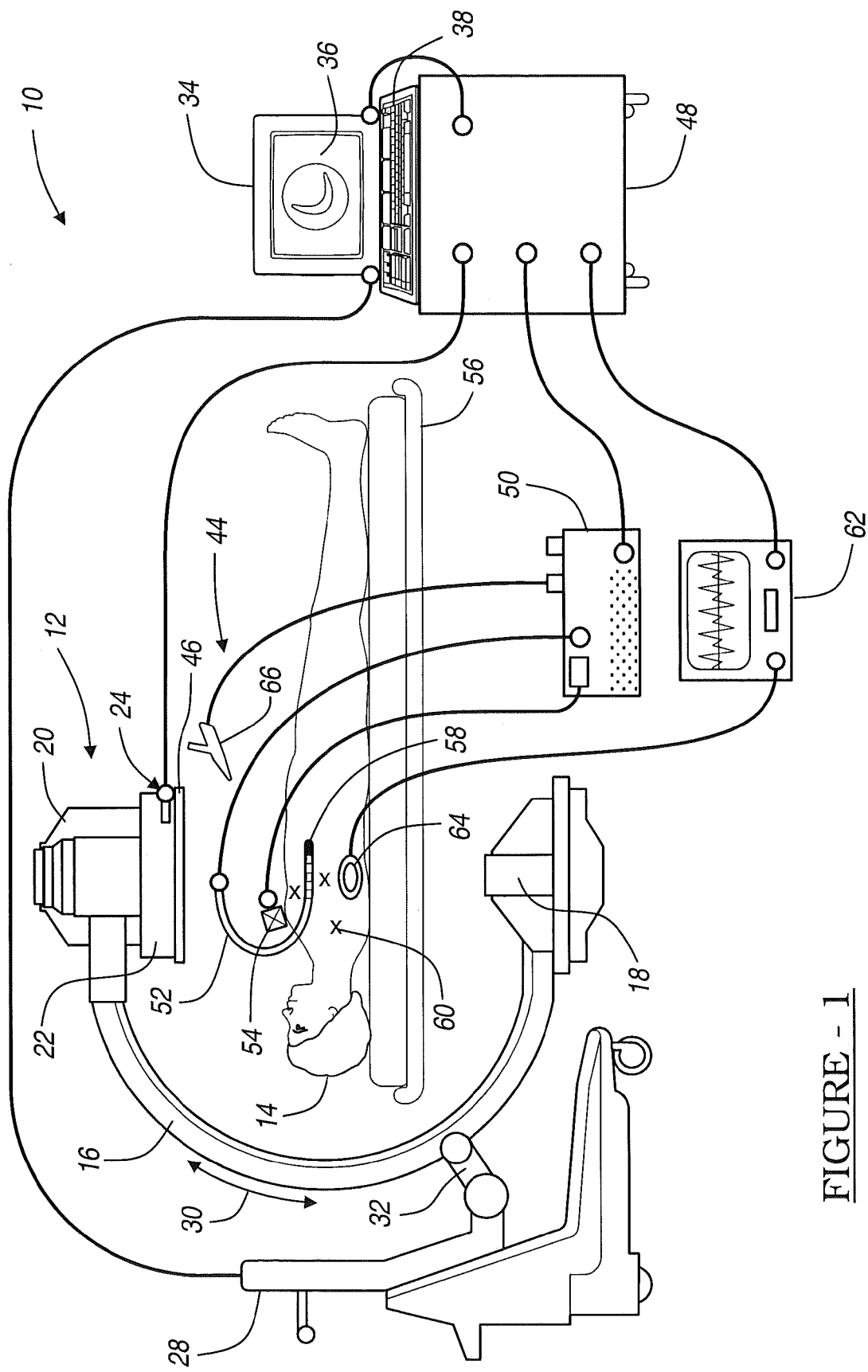
FIG. 1 is a diagram of a catheter navigation system according to the teachings of the present invention.

FIG. 1 is a diagram illustrating an overview of an image-guided catheter navigation system 10 for use in non-line-of-site navigating of a catheter during cardiac therapy or any other soft tissue therapy. It should further be noted that the navigation system 10 may be used to navigate any other type of instrument or delivery system, including guide wires, needles, drug delivery systems, cell delivery systems, gene delivery systems and biopsy systems. Moreover, these instruments may be used for cardiac therapy or any other therapy in the body or be used to navigate or map any other regions of the body, such as moving body structures. However, each region of the body poses unique requirements to navigate, as disclosed herein. For example, the navigation system 10 addresses multiple cardiac, neurological, organ and other soft tissue therapies, including drug delivery, cell transplantation, gene delivery, electrophysiology ablations, transmyocardial vascularization (TMR), biopsy guidance, and virtual echography imaging.

The navigation system 10 may include an imaging device 12 that is used to acquire pre-operative or real-time images of a patient 14. The imaging device 12 is a fluoroscopic x-ray imaging device that may include a C-arm 16 having an x-ray source 18, an x-ray receiving section 20, an optional calibration and tracking target 22 and optional radiation sensors 24. The calibration and tracking target 22 includes calibration markers 26 (see FIGS. 2a-2b), further discussed herein. A C-arm controller 28 captures the x-ray images received at the receiving section 20 and stores the images for later use. The C-arm controller 28 may also control the rotation of the C-arm 16. For example, the C-arm 16 may move in the direction of arrow 30 or rotates about the long axis of the patient, allowing anterior or lateral views of the patient 14 to be imaged. Each of these movements involve rotation about a mechanical axis 32 of the C-arm 16. In this example, the long axis of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for cardiac therapies. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking. These images are then forwarded from the C-arm controller 28 to a controller or work station 34 having a display 36 and a user interface 38. The work station 34 provides facilities for displaying on the display 36, saving, digitally manipulating, or printing a hard copy of the received images. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images. When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2B:
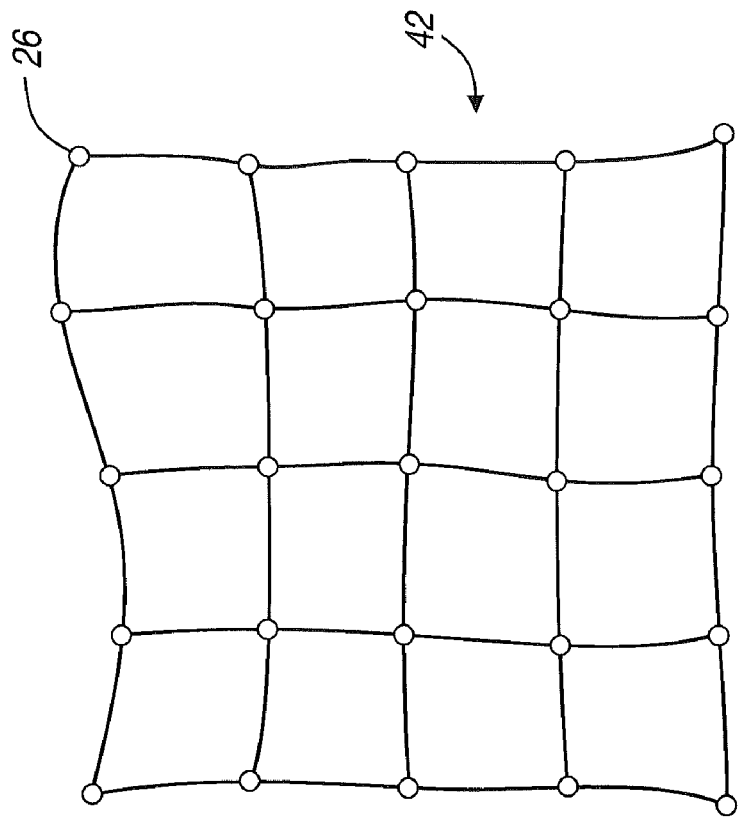
FIGS. 2a and 2b are diagrams representing undistorted and distorted views from a fluoroscopic C-arm imaging device.
Figure 2A:
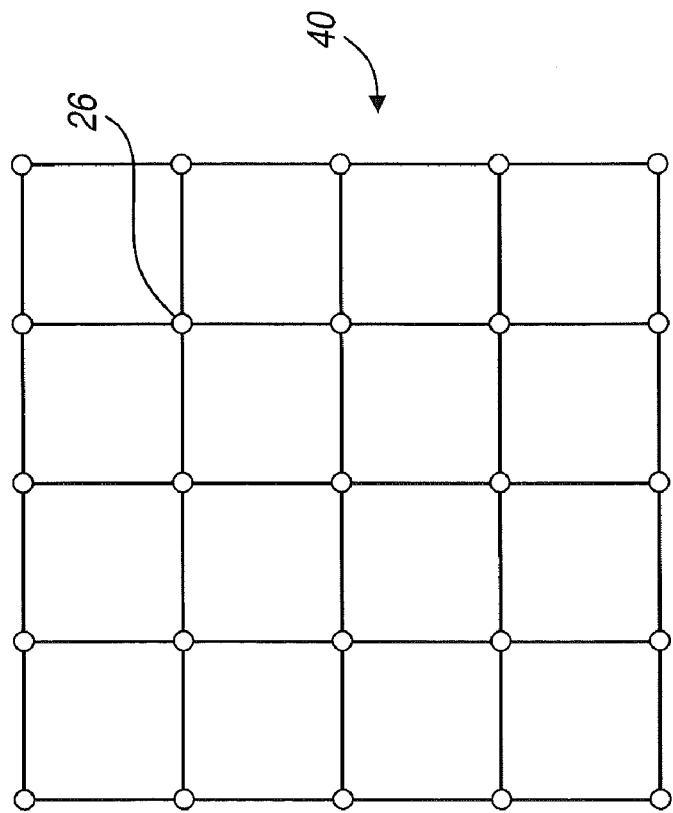

Fluoroscopic C-arm imaging devices 12 that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard arranged calibration markers 26. The image taken by the receiving section 20, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 2a). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intravascular ultrasound (IVUS), ultrasound, intra-operative CT or MRI may also be used to acquire 2D, 3D or 4D pre-operative or real-time images or image data of the patient 14. The images may also be obtained and displayed in two, three or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the heart or other areas of interest. It should further be noted that the fluoroscopic imaging device 12, as shown in FIG. 1, provides a virtual bi-plane image using a single-head C-arm fluoroscope 12 by simply rotating the C-arm 16 about at least two planes, which could be orthogonal planes to generate two-dimensional images that can be converted to three-dimensional volumetric images. By acquiring images in more than one plane, an icon representing the location of a catheter or other instrument, introduced and advanced in the patient 14, may be superimposed in more than one view on display 36 allowing simulated bi-plane or even multi-plane views, including two and three-dimensional views.

These types of imaging modalities may provide certain distinct benefits and disadvantages for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames that are discussed herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction using dynamic reference frames.

Ultrasound imaging is also generally intra-operative procedure using a non-ioning field to provide either 2D, 3D, or 4D imaging, including anatomy and blood flow information.

Ultrasound imaging provides automatic registration and does not need to account for any motion correction.

The navigation system 10 further includes an electromagnetic navigation or tracking system 44 that includes a transmitter coil array 46, the coil array controller 48, a navigation probe interface 50, an electromagnetic catheter 52 or any other type of instrument and a dynamic reference frame 54. It should further be noted that the entire tracking system 44 or parts of the tracking system 44 may be incorporated into the imaging device 12, including the work station 34 and radiation sensors 24. Incorporating the tracking system 44 will provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. However, it should be noted that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the catheter 52, further discussed herein. These induced signals from the catheter 52 are delivered to the navigation probe interface 50 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in catheter 52. Alternatively, the catheter 52 may employ a wireless communications channel as opposed to being coupled directly to the navigation probe interface 50.

The catheter 52, as will be described in detail below, is equipped with at least one, and generally multiple, localization sensors 58. The catheter 54 is also generally a steerable catheter that includes a handle at a proximal end and the multiple location sensors 58 fixed to the catheter body and spaced axially from one another along the distal segment of the catheter 52. The catheter 52, as shown in FIG. 1 includes four localization sensors 58. The localization sensors 58 are generally formed as electromagnetic receiver coils, such that the electromagnetic field generated by the transmitter coil array 46 induces current in the electromagnetic receiver coils or sensors 58. The catheter 52 may also be equipped with one or more sensors, which are operable to sense various physiological signals. For example, the catheter 52 may be provided with electrodes for sensing myopotentials or action potentials. An absolute pressure sensor may also be included, as well as other electrode sensors. The catheter 52 may also be provided with an open lumen, further discussed herein, to allow the delivery of a medical device or pharmaceutical/cell/gene agents. For example, the catheter 52 may be used as a guide catheter for deploying a medical lead, such as a cardiac lead for use in cardiac pacing and/or defibrillation or tissue ablation. The open lumen may alternatively be used to locally deliver pharmaceutical agents, cell, or genetic therapies.

In an alternate embodiment, the electromagnetic sources or generators may be located within the catheter 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation, further discussed herein. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as on the patient's chest, as shown in FIG. 1 or on the patient's back. The dynamic reference frame 54 can be affixed to the patient's skin, by way of a stick-on adhesive patch. The dynamic reference frame 54 may also be removably attachable to fiducial markers 60 also positioned on the patient's body and further discussed herein.

Alternatively, the dynamic reference frame 54 may be internally attached, for example, to the wall of the patient's heart or other soft tissue using a temporary lead that is attached directly to the heart. This provides increased accuracy since this lead will track the regional motion of the heart. Gating, as further discussed herein, will also increase the navigational accuracy of the system 10. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference. It should further be noted that multiple dynamic reference frames 54 may also be employed. For example, an external dynamic reference frame 54 may be attached to the chest of the patient 14, as well as to the back of the patient 14. Since certain regions of the body may move more than others due to motions of the heart or the respiratory system, each dynamic reference frame 54 may be appropriately weighted to increase accuracy even further. In this regard, the dynamic reference frame 54 attached to the back may be weighted higher than the dynamic reference frame 54 attached to the chest, since the dynamic reference frame 54 attached to the back is relatively static in motion.

The catheter and navigation system 10 further includes a gating device or an ECG or electrocardiogram 62, which is attached to the patient 14, via skin electrodes 64, and in communication with the coil array controller 48. Respiration and cardiac motion can cause movement of cardiac structures relative to the catheter 54, even when the catheter 54 has not been moved. Therefore, localization data may be acquired on a time-gated basis triggered by a physiological signal. For example, the ECG or EGM signal may be acquired from the skin electrodes 64 or from a sensing electrode included on the catheter 54 or from a separate reference probe. A characteristic of this signal, such as an R-wave peak or P-wave peak associated with ventricular or atrial depolarization, respectively, may be used as a triggering event for the coil array controller 48 to drive the coils in the transmitter coil array 46. This triggering event may also be used to gate or trigger image acquisition during the imaging phase with the imaging device 12. By time-gating or event gating at a point in a cycle the image data and/or the navigation data, the icon of the location of the catheter 52 relative to the heart at the same point in the cardiac cycle may be displayed on the display 36, further discussed herein.

Additionally or alternatively, a sensor regarding respiration may be used to trigger data collection at the same point in the respiration cycle. Additional external sensors can also be coupled to the navigation system 10. These could include a capnographic sensor that monitors exhaled $CO_2$ concentration. From this, the end expiration point can be easily determined. The respiration, both ventriculated and spontaneous causes an undesirable elevation or reduction (respectively) in the baseline pressure signal. By measuring systolic and diastolic pressures at the end expiration point, the coupling of respiration noise is minimized. As an alternative to the $CO_2$ sensor, an airway pressure sensor can be used to determine end expiration.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the catheter 52 or pointing device is used, the work station 34 in combination with the coil array controller 48 and the C-arm controller 28 uses the translation map to identify the corresponding point on the pre-acquired image, which is displayed on display 36. This identification is known as navigation or localization. An icon representing the localized point or instruments are shown on the display 36 within several two-dimensional image planes, as well as on three and four dimensional images and models.

To enable navigation, the navigation system 10 must be able to detect both the position of the patient's anatomy and the position of the catheter 52 or other surgical instrument. Knowing the location of these two items allows the navigation system 10 to compute and display the position of the catheter 52 in relation to the patient 14. The tracking system 44 is employed to track the catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the catheter 52 during localization and relates this spatial information to patient registration data to enable image guidance of the catheter 52 within the patient 14.

Patient registration is the process of determining how to correlate the position of the instrument or catheter 52 on the patient 14 to the position on the diagnostic or pre-acquired images. To register the patient 14, the physician or user may use point registration by selecting and storing particular points from the pre-acquired images and then touching the corresponding points on the patient's anatomy with a pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The system 10 may also perform registration using anatomic surface information or path information, further discussed herein. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, as set forth in U.S. Ser. No. 60/465,615, entitled "Method and Apparatus for Performing 2D to 3D Registration" filed on Apr. 25, 2003, which is hereby incorporated by reference. The registration process may also be synched to an anatomical function, for example, by the use of the ECG device 62, further discussed herein.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

Figure 3:
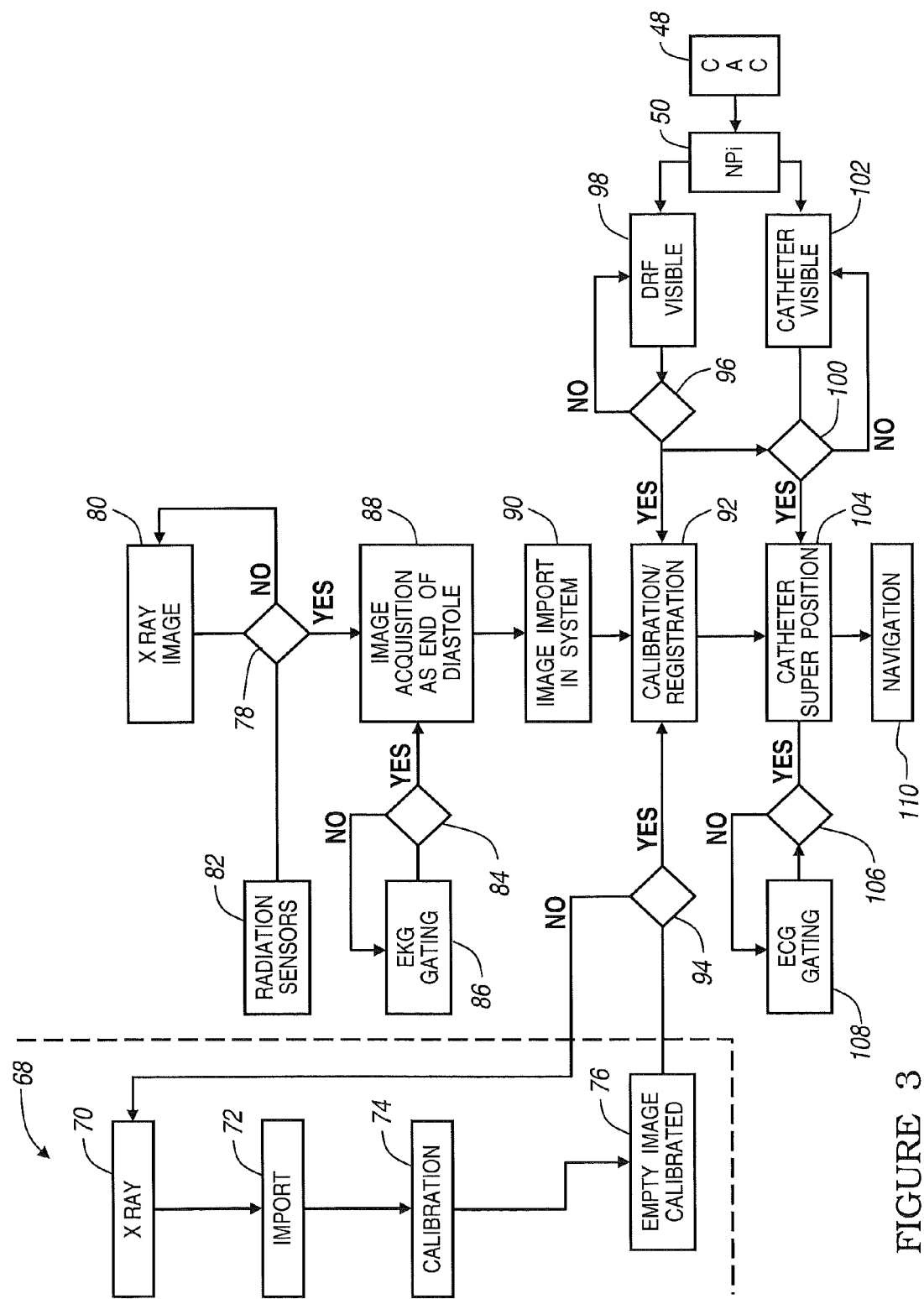
FIG. 3 is a logic block diagram illustrating a method for navigating a catheter during cardiac therapy.

Turning now to FIG. 3, a logic flow diagram illustrating an exemplary operation of the navigation system 10 is set forth in further detail. First, should the imaging device 12 or the fluoroscopic C-arm imager 12 not include a digital receiving section 20, the imaging device 12 is first calibrated using the calibration process 68. The calibration process 68 begins at block 70 by generating an x-ray by the x-ray source 18, which is received by the x-ray receiving section 20. The x-ray image 70 is then captured or imported at import block 72 from the C-arm controller 28 to the work station 34. The work station 34 performs intrinsic calibration at calibration block 74, as discussed above, utilizing the calibration markers 26, shown in FIGS. 2a and 2b. This results in an empty image being calibrated at block 76. This calibrated empty image is utilized for subsequent calibration and registration, further discussed herein.

Once the imaging device 12 has been calibrated, the patient 14 is positioned within the C-arm 16 between the x-ray source 18 and the x-ray receiving section 20. The navigation process begins at decision block 78 where it is determined whether or not an x-ray image of the patient 14 has been taken. If the x-ray image has not been taken, the process proceeds to block 80 where the x-ray image is generated at the x-ray source 18 and received at the x-ray receiving section 20. When the x-ray source 18 is generating x-rays, the radiation sensors 24 identified in block 82 activate to identify that the x-ray image 80 is being taken. This enables the tracking system 44 to identify where the C-arm 16 is located relative to the patient 14 when the image data is being captured.

The process then proceeds to decision block 84 where it is determined if the x-ray image acquisition will be gated to physiological activity of the patient 14. If so, the image device 12 will capture the x-ray image at this desired gating time. For example, the physiological change may be the beating heart, which is identified by ECG gating at block 86. The ECG gating enables the x-ray image acquisition to take place at the end of diastole at block 88 or at any other cycle. Diastole is the period of time between contractions of the atria or the ventricles during which blood enters the relaxed chambers from systemic circulation and the lungs. Diastole is often measured as the blood pressure at the instant of maximum cardiac relaxation. ECG gating of myocardial injections also enables optimal injection volumes and injection rates to achieve maximum cell retention. The optimal injection time period may go over one heart cycle. During the injection, relative motion of the catheter tip to the endocardial surface needs to be minimized. Conductivity electrodes at the catheter tip may be used to maintain this minimized motion. Also, gating the delivery of volumes can be used to increase or decrease the volume delivered over time (i.e., ramp-up or ramp-down during cycle). Again, the image may be gated to any physiological change like the heartbeat, respiratory functions, etc. The image acquired at block 88 is then imported to the work station 34 at block 90. If it is not desired to physiologically gate the image acquisition cycle, the process will proceed from the x-ray image block 80 directly to the image import block 90.

Once the image is received and stored in the work station 34, the process proceeds to calibration and registration at block 92. First, at decision block 94, it is determined whether the imaging device 12 has been calibrated, if so, the empty image calibration information from block 76 is provided for calibration registration at block 92. The empty image calibration information from block 76 is used to correct image distortion by establishing projective transformations using known calibration marker locations (see FIGS. 2a and 2b). Calibration registration 92 also requires tracking of the dynamic reference frame 54. In this regard, it is first determined at decision block 96 whether or not the dynamic reference frame is visible, via block 98. With the dynamic reference frame 54 visible or in the navigation field and the calibration information provided, the work station 34 and the coil array controller 48, via the navigation probe interface 50 performs the calibration registration 92 functions. In addition to monitoring the dynamic reference frame 54, the fiducial array or landmarks 60 may also be used for image registration.

Once the navigation system 10 has been calibrated and registered, navigation of an instrument, such as the catheter 52 is performed. In this regard, once it is determined at decision block 100 that the catheter 54 is visible or in the navigation field at block 102, an icon representing the catheter 52 is superimposed over the pre-acquired images at block 104. Should it be determined to match the superimposed image of the catheter 52 with the motion of the heart at decision block 106, ECG gating at block 108 is performed. The catheter 52 may then be navigated, via navigation block 110 throughout the anatomical area of interest in the patient 14.

Figure 4:
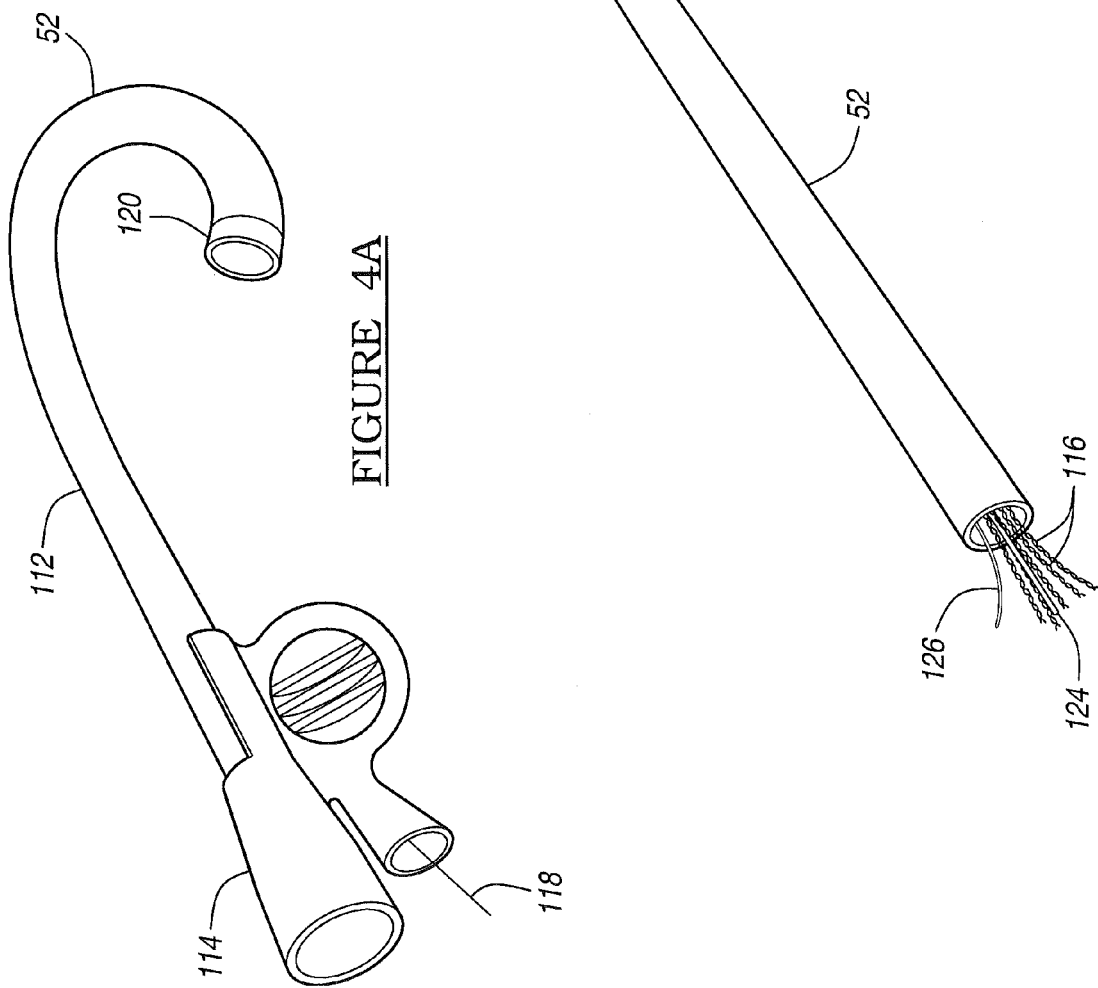
FIGS. 4a and 4b are side partial cross-sectional views of a navigable catheter employed in cardiac therapies according to the teachings of the present invention.
Figure 5:
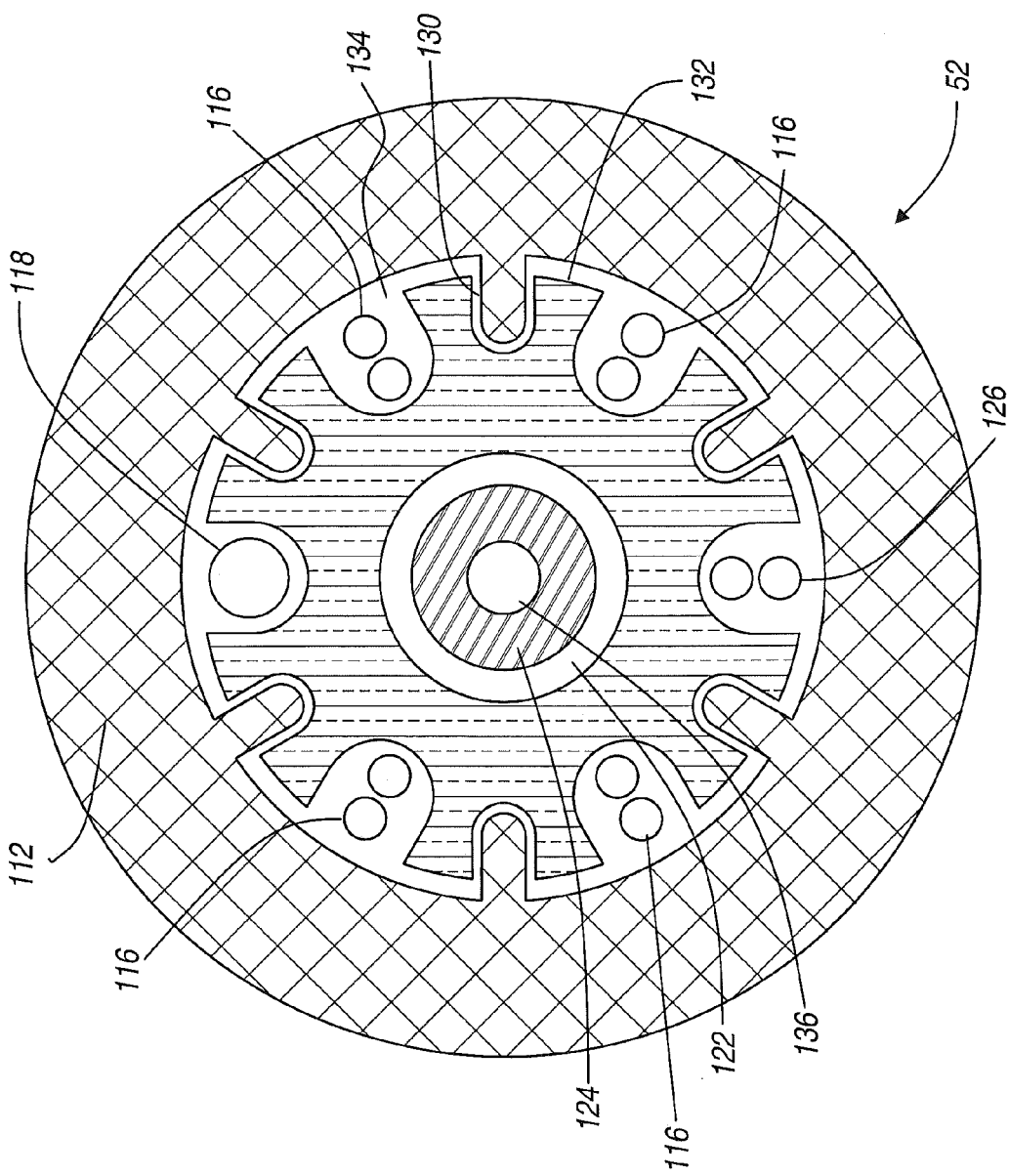
FIG. 5 is an axial cross-section view of the navigable catheter shown in FIGS. 4a and 4b.

Turning to FIGS. 4-5, an exemplary catheter 52 is shown in further detail. The exemplary catheter, as shown in FIG. 4a, includes an external flexible body 112 and a proximal handle 114. Positioned within the catheter 52 are the four sensing coils 58 disposed distally in the catheter 52. The localization or sensing coils 58 are multi-layer and multi-turn coils, which are coupled to four sets of twisted pair conductors 116. The catheter 52 further includes a pull wire 118, which is used to control and guide the distal tip 120 of the catheter 52. Extending through the catheter 52 is a central lumen 122 that can be used to deliver and transport cells or drug therapy and leads for cardiac pacemakers. The central lumen 122, shown in FIG. 4b retains a hypodermic needle 124 that can be used as the delivery instrument. The catheter 52 further includes electrode conductors 126 and an electrode tip ring 128 used to sense various electrical signals from the heart. Other sensors that can be attached to the catheter 52 include multiple electrode sensors, absolute pressure sensors, accelerometers and oxygen saturation sensors. For mapping catheters 52, micromotion arrays, further discussed herein, may also be embedded to electronically control curvature of the catheter 52 to provide a semi-automated mapping procedure.

Turning to FIG. 5, the axial cross-section of the catheter 52 is shown in further detail. The catheter 52 is again formed from the outer cover 112 that is formed from an extruded polymer having six directional splines 130. An internal extrusion 132 defines six chambers or lumens 134 between the internal extrusion 132 and external extrusion 112. Within four of the chambers 134 are the four twisted pair conductors 116, which are coupled to each of the coils or sensors 58. Located in another chamber 132 are the electrode conductors 126. The pull wire 118 is located in the remaining chamber 132. By adjusting the pull wire 118 along with the torque transferring splines 130, the directional catheter 52 can be positioned and steered as desired. Also, located within the center of the catheter 52 is the lumen 122 housing the hypodermic needle 124 having a central port 136 for passing cells, catheter leads and other items. Further details of the catheter 52, as well as other embodiments of the catheter 52 are set forth in U.S. Ser. No. 10/299,484, entitled "Multi-Lumen Body for Medical Catheter and Leads," naming as inventors Kenneth Gardeski, Michael Leners and Jesus Casas-Bejar, filed Nov. 19, 2002, which is hereby incorporated by reference. Again, the catheter 52 may include a lumen 122 open on both ends, which allows it to be used to deliver several cardiac therapies (e.g., to implant pacing leads, deliver drugs, to transplant cells into the myocardium, or to perform complex electrophysiological procedures, including ablation).

The navigation system 10 enhances minimally invasive cardiac therapies by making the procedure more intuitive. The catheter 52 can be used to implant pacing leads, perform cell transplantation, deliver drugs or perform ablations. The catheter 52 having navigation guidance, via sensors 58 provides enhanced outcomes by making lead placement more successful in difficult anatomies, by insuring cells are transplanted in the most viable myocardium within the infarct, etc. Moreover, use of the electrocardiogram device 62 enables further gating of the drug deliver and cell delivery at the most optimum times for providing additional capabilities to the navigation system 10. The navigation system 10 can also be applied to non-cardiac therapies, such as neuro-vascular catheters, or oncology drug delivery applications, based on combined PET/CT (functional and anatomical) pre-operative data or pre-operative data from any other bio-imaging system for tumor identification and location. The navigation system 10 can also map on the display 36 the delivery of cell or drug therapy or other therapies that are annotated on 2D, 3D or 4D images or graphic displays. The navigation system 10 may also generate distribution maps on how the cell or drug delivery or other therapies are disbursed through the region of interest, such as the heart. These iso-contours or iso-dose contours display how therapy is disbursed through the tissue. For example, a bullseye type graphic may be displayed on the three-dimensional heart model with different concentric rings having different colors identifying the amount of drug therapy delivered to the noted regions.

The navigation system 10 can also be used and employed in several types of medical procedures and has several improvements and advantages over existing systems. The navigation system 10 provides application and methods for electromagnetic non-line-of-site navigation for catheter delivery of pacing leads. The navigation system 10 includes heuristics that are integrated into the software of the work station 34 to provide an algorithm for locating the coronary sinus, further discussed herein. The navigation system 10 provides for gating or timing of injections for cell transplantation in the infarcted myocardium as a substitute for anchoring. The cell delivery imaging modality is generally utilized as real-time MR. Real time MR allows catheter navigation while visualizing the infarcted region of the heart. Use of pre-operative profusion MR images may also be used to clearly identify the infarct region, along with the quality of the infarct. The navigation system 10 also includes integrated programming functions in the work station 34 that are used to help identify optimum pacing sites, further discussed herein. Also, the navigation system 10 provides a simulated bi-plane or multi-plane fluoroscopy for cardiac applications with one-head systems and also catheter registration to the images, whether fluoroscopic or volume-rendered using MR, CT, and moving surfaces.

Figure 6:
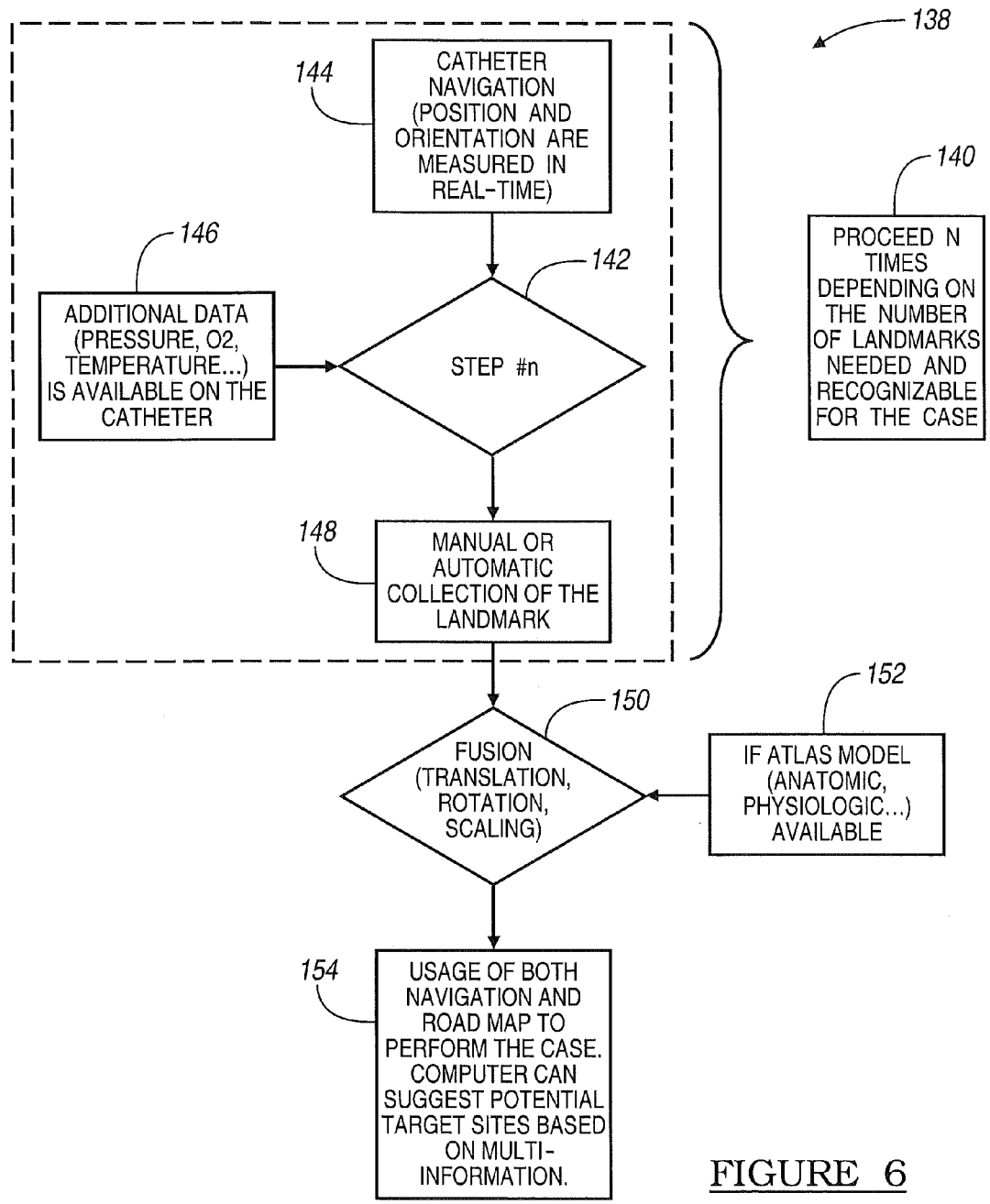
FIG. 6 is a logic block diagram illustrating a method for navigating and accessing a statistical atlas and employing the atlas for target suggestions according to the teachings of the present invention.

Turning now to FIG. 6, an exemplary lead implant procedure 138 is shown in detail. While this procedure is described regarding implanting a lead for a pacemaker, it should again be noted that this process can be applied to any type of cardiac therapy as discussed herein, such as angioplasty, stenting, and ablation. The lead placement procedure disclosed herein is designed to reduce the procedure time and reduce the procedure costs and enable a physician to implant a lead quicker, safer and in a more precise optimized location. Delivery catheters 52 are, therefore, very important with cardiac resynchronization therapy. The catheter 52 and fluoroscopic images are used to find and cannulate the coronary sinus. Once cannulated, a lead is delivered through the catheter 52 and into the cardiac veins.

Various types of catheters 52 may be utilized to deliver a lead to the desired cardiac location, via the central port 136 in the hypodermic needle 124. The catheter 52 may include the catheter electrode 128, which could be used to monitor the intra-cardiac electrical signals. Since each region in the heart has characteristic differences, these differences can be used to distinguish which region the catheter tip 120 is placed within the heart. In addition to monitoring intra-cardiac electrical signals, electrical impedance (high and low frequency) may also be monitored, via the electrode 128. This could be monitored continuously to highlight the cardiac impedance cycle. In this regard, it is believed that each region within the heart has an unique cardiac impedance and will have distinct characteristics. The cardiac impedance would, therefore, provide more information to be correlated with the sensors 58 and the catheter 52 in determining the location of the lead tip and can act as an anatomical landmark. The impedance signal could also be used to help determine if the lead is floating or lodged against the heart tissue.

Another type of sensor, which can be placed at the tip of the catheter 52 is an absolute pressure sensor, which can monitor hemo-dynamics. The intra-cardial pressure signal is an important signal in diagnostics and critical care monitoring. As a consequence, the characteristics of the pressure signal are well characterized for each region of the heart. For normal hearts, each region is distinctly characteristic with the sharp transitions between the upper and lower chambers of the heart. Taken with the electrode sensors 58 information, the location of the catheter tip 120 can be determined with a further high degree of confidence. These transition regions between the chambers of the heart could also be used as registration data points for 3-D heart models, further discussed herein.

The fluoro-enhanced implant procedure provides the physician with real-time location information of the catheter 52. An icon representing the catheter 52 is superimposed on the background of a 3-D heart model or atlas model. The electrode and/or pressure sensor information discussed above is used to correctly locate the catheter position within this heart model. In this regard, very specific locations can be searched out to provide reference points within the heart to fit the model space. The transition between regions of the heart are easily identified through changes in the morphology of the electrode and pressure signals. The transition regions are very sharp, making these regions excellent reference points or landmarks for the heart model. The possible reference points include the superior vena cava (SVC) to right atria transition, the tricuspid valve, and the left ventricular apex. As these reference points are located, the heart model is shrunk or stretched and rotated to match these reference points. Normally, the navigation system 10 will automatically locate the reference points by monitoring the electrode and pressure sensors. This results in a visualization of the catheter 52 as it is moved through the heart model. Once the 3-D heart model placement is established, a mapping function can begin or a lead implant site chosen. The 3-D heart model will be scaled and rotated only within physiological bounds. Reference points outside of these bounds will generate an alert and require the physician to resolve the discrepancy.

An exemplary lead implant method or procedure 138 for identifying a lead implant site is illustrated in FIG. 6. The procedure 138 includes a landmark identification process 140 that includes n number of steps at block 142, which depends on the number of landmarks needed or recognizable for a particular application. Included in this process 140 is catheter navigation, via block 144, which provides position and orientation information that is measured in real time, via the sensors 58 within catheter 52. As the catheter 52 is navigated, as set forth in block 144, additional data is gathered within the heart, via sensors positioned on the catheter 52 at block 146. As discussed, this additional data can include pressure, temperature, oxygen, impedance and electro-physiological information. By monitoring this additional data at block 146, landmarks or reference points within the heart can be identified and marked on the catheter fluoroscopic images at block 148. The process of collecting the landmarks can be a manual or automatic process by identifying the physical landmarks within the fluoroscopic image, based upon the received data from block 146, that identify distinct points or regions within the heart.

Once the multiple landmarks or reference points are identified in the heart, a 3-D heart model or atlas heart model is superimposed over the fluoroscopic images or modeled as a 3-D volume view by registering or translating the 3-D heart model in relation to the landmarks collected at block 148. This fusion occurs at block 150, which translates, rotates and scales the 3-D heart model, based upon the collected landmarks to provide a patient specific heart model that can be used for various procedures. Again, the heart model can be generated from an atlas model, as set forth in block 152 or it may be generated from an actual physiological image, such as from an MRI or a CT. Once the 3-D model has been scaled and registered to the landmarks, the controller or work station 34 provides navigation and road map information to direct the catheter 52 through the heart to a suggested or estimated optimized target site for lead placement at block 154. This target site can be identified on the 3-D model along with a real time view of an icon representing the catheter 52 moving toward the suggested target site. In this regard, the physician would know where the target is on the 3-D map or display 36 and can simply navigate the catheter 52 toward this target. The target site can be based on statistical maps that can suggest where lead placement should take place, depending on the pathology of the patient.

In addition to identifying a potential target site for lead placement, the navigation system 10 can also suggest sites for drug or cell delivery. Alternatively, the catheter 52 can be used as a mapping catheter 52. The position sensors 58 provide real time feedback on the catheter location in 3-D space, which is a requirement for accurate mapping. The mapping procedure is essentially an extension of the fluoro-enhanced implant approach, set forth in FIG. 6. The mapping catheter 52 will be optimized for mapping and/or to implant, but the basic procedure remains the same.

Essentially, the 3-D heart model is calibrated using the same technique as shown in FIG. 6, and the correctly scaled heart model becomes the basis for the initial mapping grid. With a micro-motion catheter, further discussed herein, the catheter is positioned at each mapping site in a semi-autonomous fashion with user intervention as needed. For catheters without micro-motion, the system would highlight on the display 36, the next mapping point, along with the actual catheter position. The user or physician would then manually manipulate or steer the catheter tip 120 to the identified location. Alternatively, the physician or user may choose each location and initiates a mapping measurement for that point. With a single electrode catheter 52, the intrinsic electrical amplitude, pacing threshold, and wall motion (contractility) can be measured. As the mapping progresses, a 3-D diagnostic map of the measured parameters are displayed alongside the 3-D model display. This method of mapping provides the capability of highlighting and detailing a number of heart defects, such as chronic infarct, chronic ischemia, perfusion defect, or aneurism. If a mapping or EP catheter 52 with multiple electrodes is used, such as electrode 128, this mapping system can generate and display inter-cardiac electrical activity and timing, along with exact catheter tip and electrode location in real time. The result is a 3-D electro-anatomical map reconstruction. The applications for this system includes mapping of ventricular and supra-ventricular arrhythmias, mapping of myocardial potential and conduction velocity, and depolarization mapping. Using multiple position sensors 58, with each sensor 58 associated with an electrode on the catheter 52, the navigation system 10 can be used to accurately measure the location of each electrode measurement providing improved mapping accuracy.

In addition to using a guide wire 118 to adjust or steer the catheter 52, micro-motion technology may also be used to precisely steer the catheter in an automated manner. In this regard, selective heating of a shaped memory metal enables and provides the ability to steer the catheter 52 or lead to a precise location. The micro-motion technology applies a VLSI film to a piece of shape memory metal to form an actuator. The VLSI film has a pattern of resistors in the range of 100-300 ohms. The film is attached to the metal and the electrode connections made to the computer controller, such as the work station 34. A small amount of current is applied to one or multiple resistors, which generates a localized heating of the metal. This provides precise steering to a specific location within the heart. Also, a semi-automated mapping procedure can then take place to construct the electro-anatomical maps. In this regard, the micro-motion actuator is used to manipulate the catheter 52 to a desired set of mapping points automatically. With the addition of position sensors 58, real time feedback of the catheter curvature provides improved steering capabilities. Should it be desired, strain gages may also be applied to the actuator to provide additional real time feedback of the curved position. For example, micro-motion technology is available from Micro-Motion Sciences, which provides a controllable and steerable catheter, via the selective heating of a shaped memory metal that passes through the catheter 52. Micro-electron mechanical sensor (MEMS) technology, as well as nano technology may also be utilized for controlling the manipulation and steering of the catheter 52.

Again, fluoro pre-imaging of the patient is initially completed using the imaging system 12. Once completed, the navigation system 10 utilizes a three-dimensional volume rendered or wire frame model of the heart or other soft tissue that is registered to the patient 14. The heart model is scalable, morphed or registered using 2-D and 3-D image techniques to match the fluoro images and measured reference points are determined from the transitional signals on the electrical and pressure sensors associated with the catheter 52. The navigation system 10 then displays the three-dimensional heart model on the display 36. An icon of the catheter 52 is simultaneously displayed in correct relation to the model and fluoro images. As the session begins, the model is positioned based on the known placement of the dynamic reference frame 54 and the fluoro images captured by the imager 12. Once the catheter 52 is in range, it is displayed on the display 36 relative to the rendered heart model. Simultaneously, multiple views of the catheter 52 and heart model are available on the display 36 to aid in visualizing the catheter shape and position within the heart.

During the initial model scaling, the electrical and pressure signals are continuously monitored and displayed. At the transition from the superior vena cava to the right atrium, the electrical and pressure signal morphology changes. This transition is noted by the navigation system 10, along with the catheter position at the time of the transition. This position represents a reference point for the heart model. The heart model is then repositioned to match this reference point. The physician is given full control over this process. If necessary, the physician can manually set any of the heart model reference points. This is accomplished by manually placing the catheter 52 at the desired reference position and selecting the appropriate model reference point. This same process is repeated as the catheter 52 passes the tricuspid valve and into the right ventricle. This transition point marks an additional reference point for the model. At these reference positions, the model is stretched, rotated, and aligned to match the reference locations. A third reference point is the left ventricular apex. At this point, the physician should be able to easily manipulate the catheter 52 into the apex or mark this as a reference point.

At this point, the navigation system 10 displays a very accurate visual representation of the catheter placement within the heart model. The visual feedback allows the position and orientation of the catheter 52 to be manipulated with a high degree of confidence and accuracy. The 3-D model includes statistical atlas information that can be provided to the physician for improved outcome. The potential implant sites can be tested for good electrical characteristics and optimal sites selected. The catheter 52 is then used to guide the lead to the chosen site. A final fluoroscopic image can then be taken to assess excessive lead motion and lead tension.

It should also be noted that as long as the dynamic reference frame 54 is not moved, the catheter 52 can be re-introduced without needing to rescale the 3-D heart model. The calibration of the heart model is maintained. In this same way, a secondary catheter could be introduced with no loss and accuracy. Once the 3-D heart model is scaled and positioned, it remains accurate throughout the procedure.

Figure 7:
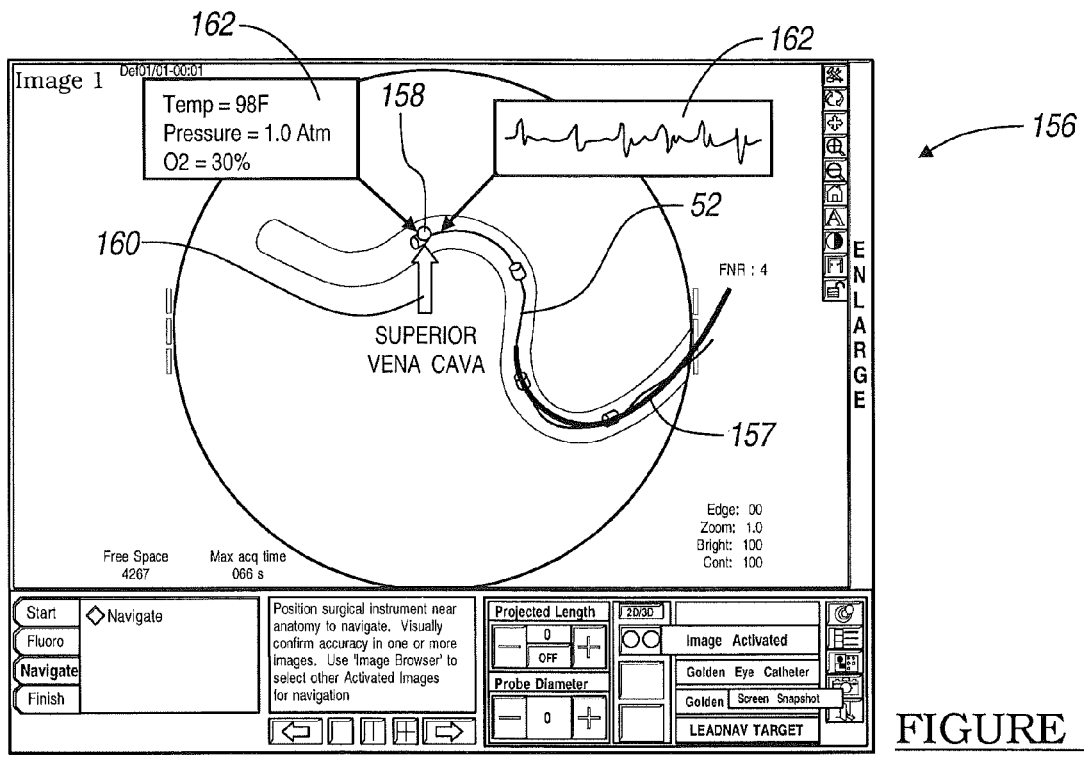
FIG. 7 is a figure of a display illustrating data available for a landmark accessible by a user of the system.

Referring to FIG. 7, an exemplary image 156 that is displayed on display 36 is illustrated. In the image 156, an icon 157 representing the position and location of the catheter 52 is shown navigating through the superior vena cava. In order to provide a road map to guide or suggest a possible path for the catheter 52, a target 158 may be illustrated and superimposed onto the pre-acquired image, as shown at reference numeral 158. At this specific landmark 158, data can either be manually or automatically downloaded from other sources, such as the catheter, lead, or pacemaker programmer to create a hyperlink with this virtual annotated landmark 158. By a simple mouse click (red arrow 160), all available data could be displayed by a pop-up window 162. This data includes information, such as temperature, pressure, oxygen level, or electro-physiological signals, as shown in windows 162. As such, a user or physician would simply refer to the virtual annotated landmarks 158 in the particular view and click on that landmark 158 to obtain the physiological information at that particular site. The catheter 52 will thus gather, store, and download data on patient morphology, electrical thresholds and other implant parameters that can be stored for later review.

The catheter 52 may also optionally be fitted with a fiberoptic imaging sensor. Fiberoptic imaging technology is available, for example, from Cardio Optics of Boulder, Colo., which enables a catheter to view the heart and heart structures continuously through blood. This enables the physician or user to have an additional view of what is in front of the catheter 52, which can be displayed on display 36.

Figure 8:
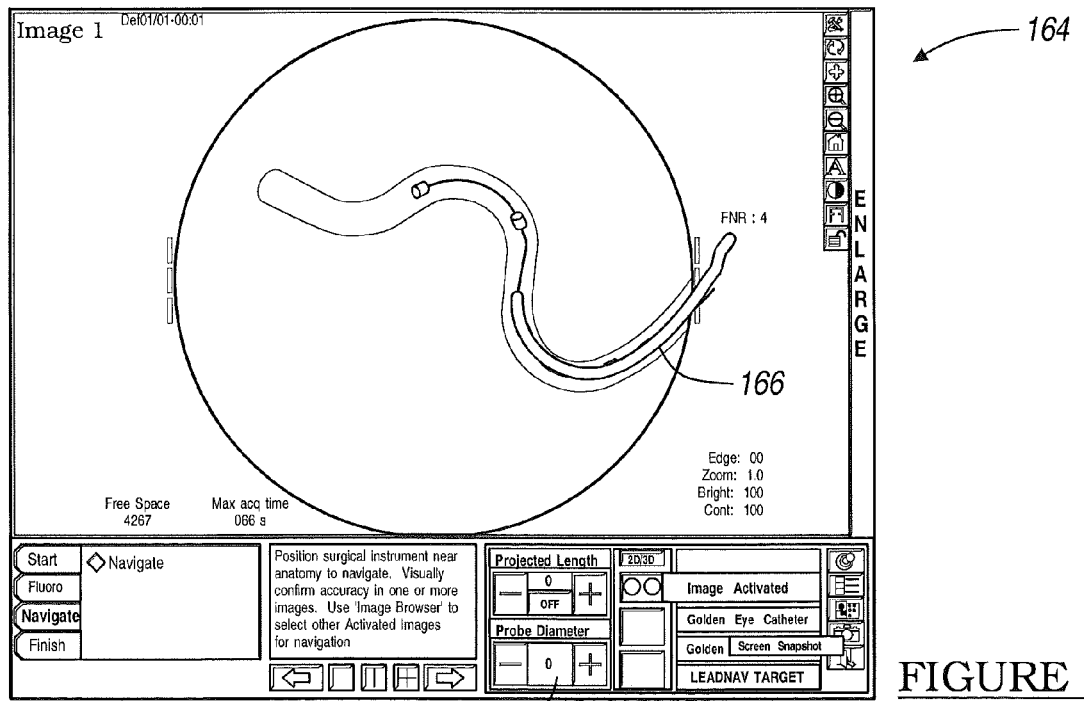
FIG. 8 is a figure of a display illustrating an adjustable icon or probe diameter.

Turning to FIG. 8, an additional exemplary image 164 that is displayed on display 36 is illustrated. The image 164 includes an icon 166, representing the position and location of the catheter 52. The icon 166 has an enlarged probe diameter as compared to the icon 157, shown in FIG. 7. This probe diameter of the icon 166 representing the catheter 52 is adjusted by way of probe diameter adjustment switches 168. By pressing the "+" button of the probe diameter switches 168, the probe diameter increases. Conversely, by pressing the "−" button, the probe diameter decreases. This enables the surgeon to adjust the probe diameter to a desired size providing further or enhanced visualization of the surgical procedure.

Figure 9:
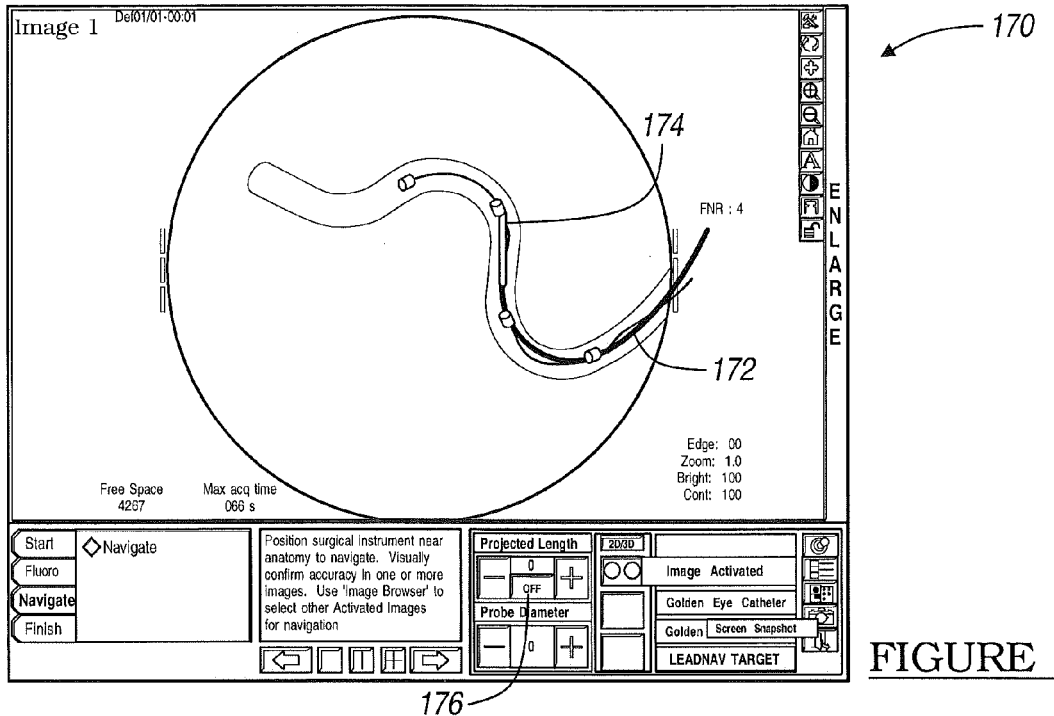
FIG. 9 is a figure of the display illustrating a straight projection along a direction of a first sensor in the navigable catheter.

Referring now to FIG. 9, an exemplary image 170 that is displayed on display 36 is illustrated. The image 170 includes an icon 172 representing the location and position of the catheter 52. The icon 172 further includes a straight projection portion 174 that projects straight along the direction of the first sensor 58 within the catheter 52. This straight projection 174 represents a straight projected trajectory of the catheter 52. The length of the projected icon portion 174 may be adjusted via projected length switches 176. Here again, the "+" button lengthens the straight projected icon 174, while the "−" button shortens the projected length of the icon 174. This estimated straight trajectory enables the surgeon to determine where the catheter 52 is traveling and how far or how much travel is necessary to reach a desired target along a straight path.

Figure 10:
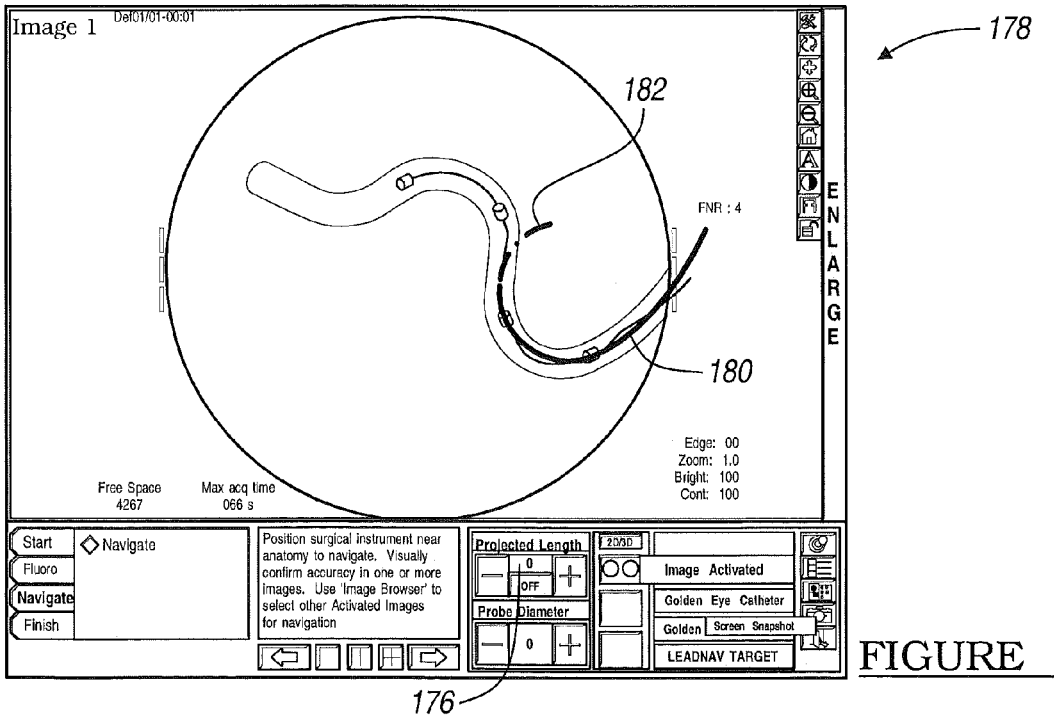
FIG. 10 is a figure of the display illustrating a splined projection or trajectory based on a shape of a curve of the navigable catheter.

Turning now to FIG. 10, an exemplary image 178 that is displayed on display 36 is illustrated. The image 178 includes an icon 180 representing the position and location of the catheter 52. The image 178 further includes a spline or curved projection 182, which is based upon the shape of the curved catheter 52, shown as icon 180. Here again, the projected length of the spline projection 182 is controlled by way of the projected length switches 176. This estimated curve projection enables the surgeon to determine where the catheter 52 will travel if the catheter 52 continues along its curved trajectory, further providing enhanced features for the surgeon navigating the catheter 52. The estimated curve is determined by use of known curve fitting algorithms that are adjustable based upon the type of catheter used and based upon the flexibility and material of the catheter 52. This enables estimated curved trajectories of the catheter 52 to be displayed to assist the user.

Figure 11:
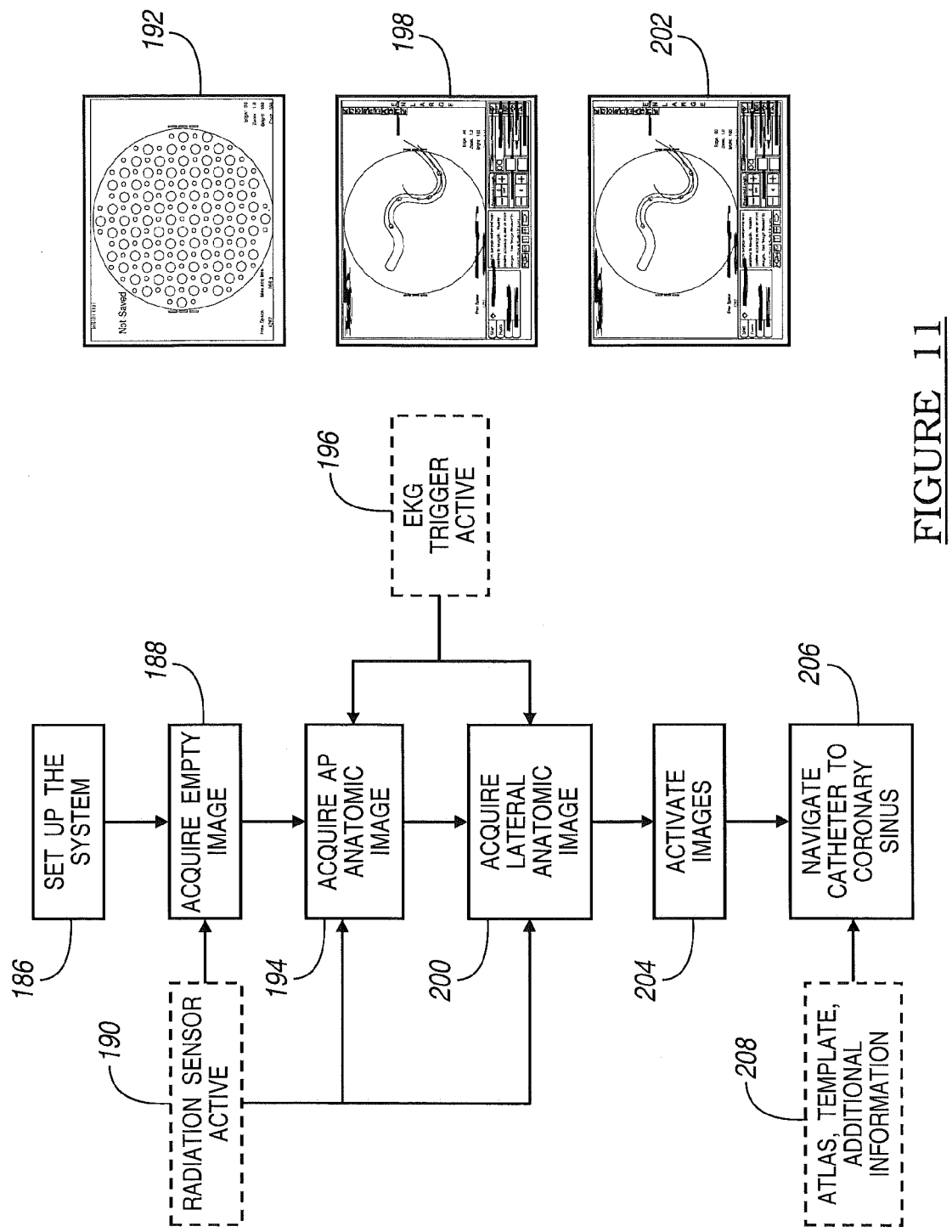
FIG. 11 is a logic block diagram illustrating a method for navigating the coronary sinus region of the heart.

Referring now to FIG. 11, an exemplary method or procedure 184 for navigating the catheter 52 to the coronary sinus region of the heart is illustrated. The procedure 184 begins at block 186, where the catheter navigation system 10 is set up. This set up includes connecting all of the appropriate hardware within the navigation system 10, as well as activating the various computers within the system 10. Once the navigation system 10 is set up at block 186, the procedure 184 proceeds to acquire an empty image at block 188. The acquisition of the empty image of the block 188 is similar to the calibration process 68, shown in FIG. 3. In this regard, an x-ray is taken by the imaging device 12 where intrinsic calibration is performed on this empty image to calibrate the imaging device 12. Radiation sensor 24 senses when the x-ray process has taken place at block 190. The resulting empty x-ray image is shown on display 36 and illustrated at block 192, which illustrates the calibration and tracking target 22. Again, the calibration process is an optional process depending on the medical procedure conducted or depending on the type of imaging system 12.

Once the navigation system 10 has been calibrated, the patient 14 is positioned within the imaging device 12 to capture various views of the patient 14. At block 194, an anterior/posterior anatomic image of the patient 14 is acquired by the imaging device 12. The image acquisition at block 194 may be gated via block 196 using the ECG 62 to trigger when the acquisition of the anterior/posterior image is acquired. The image acquisition may also be gated by any other physiological event. The anterior/posterior anatomic image of the coronary sinus region is shown at display 198. Once the anterior/posterior image is acquired at block 194, the lateral anatomic image of the patient 14 is acquired at block 200. Again, this image acquisition at block 200 may be gated, via block 196. The lateral image is shown in display block 202.

Figure 12:
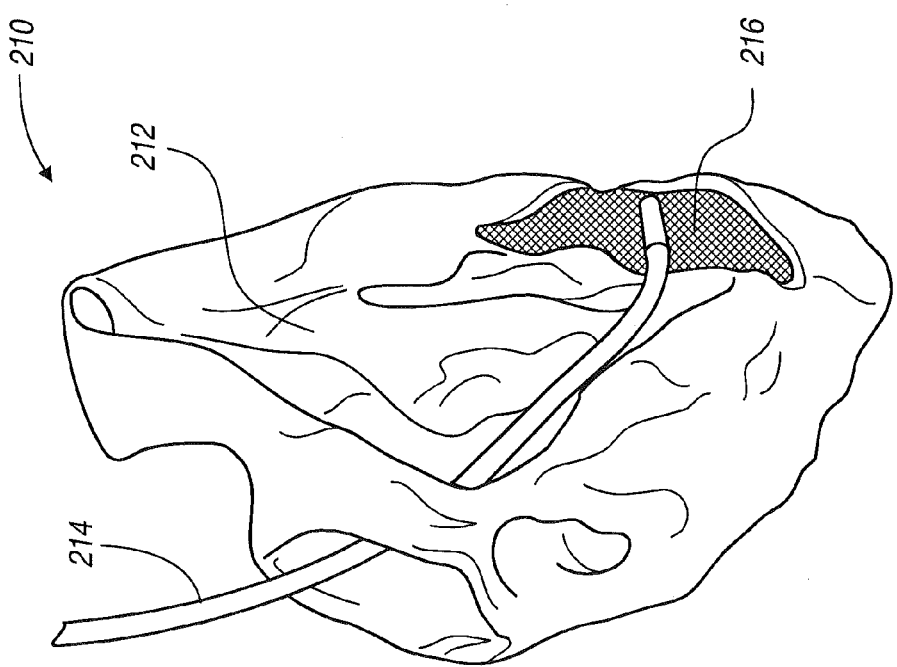
FIG. 12 is an image of a three-dimensional heart model used for cardiac therapy.

Once the anterior/posterior anatomic image is acquired at block 194 and the lateral anatomic image is acquired at block 200, the procedure 184 proceeds to block 204 where the acquired images are activated. In this regard, each image is displayed on display 36 as is shown in blocks 198 and 202. Once the images have been activated at block 204, the procedure proceeds to block 206, where the catheter 52 is navigated to the coronary sinus. To assist in this navigation of the catheter 52, atlas, template and additional information, via block 208 may be provided. The atlas information may include registering a three-dimensional atlas heart model, as shown in FIG. 12, similar to the way discussed in FIG. 6, to assist in navigating the catheter 52 to the coronary sinus. Templates may also be superimposed over the images 198 and 202 or over the three-dimensional heart model to provide a map for steering and guiding the catheter 52 through the coronary sinus region. The additional information provided at block 208 can also include an algorithm that is designed to direct the surgeon through various steps suggesting or estimating where the surgeon should be looking to guide the catheter 52 through the coronary sinus region. These steps may include providing various guide points within the template that identify on the display 36 where the catheter 52 should be navigated. As the catheter 52 reaches a particular suggested guide point, the system 10 can then prompt the surgeon to then go to the next guide point, thereby providing a roadmap to the surgeon through the coronary sinus region. The algorithm for locating the coronary sinus can increase the accuracy of pacing lead placement significantly, thereby providing reduced surgical time and increased accuracy and efficiency.

Referring to FIG. 12, an image 210 illustrating a three-dimensional atlas heart model 212 is illustrated. In the image 210, an icon 214 of the catheter 52 is illustrated passing through the heart model 212 to a cell delivery region 216. The region 216 can be highlighted on the heart model 212 to guide the surgeon to a particular region of the heart and, in this example, for cell delivery therapy. Again, the heart model 212 can also be used for any other cardiac procedure to assist the surgeon during pacing lead placement, ablation, stenting, etc.

Figure 13:
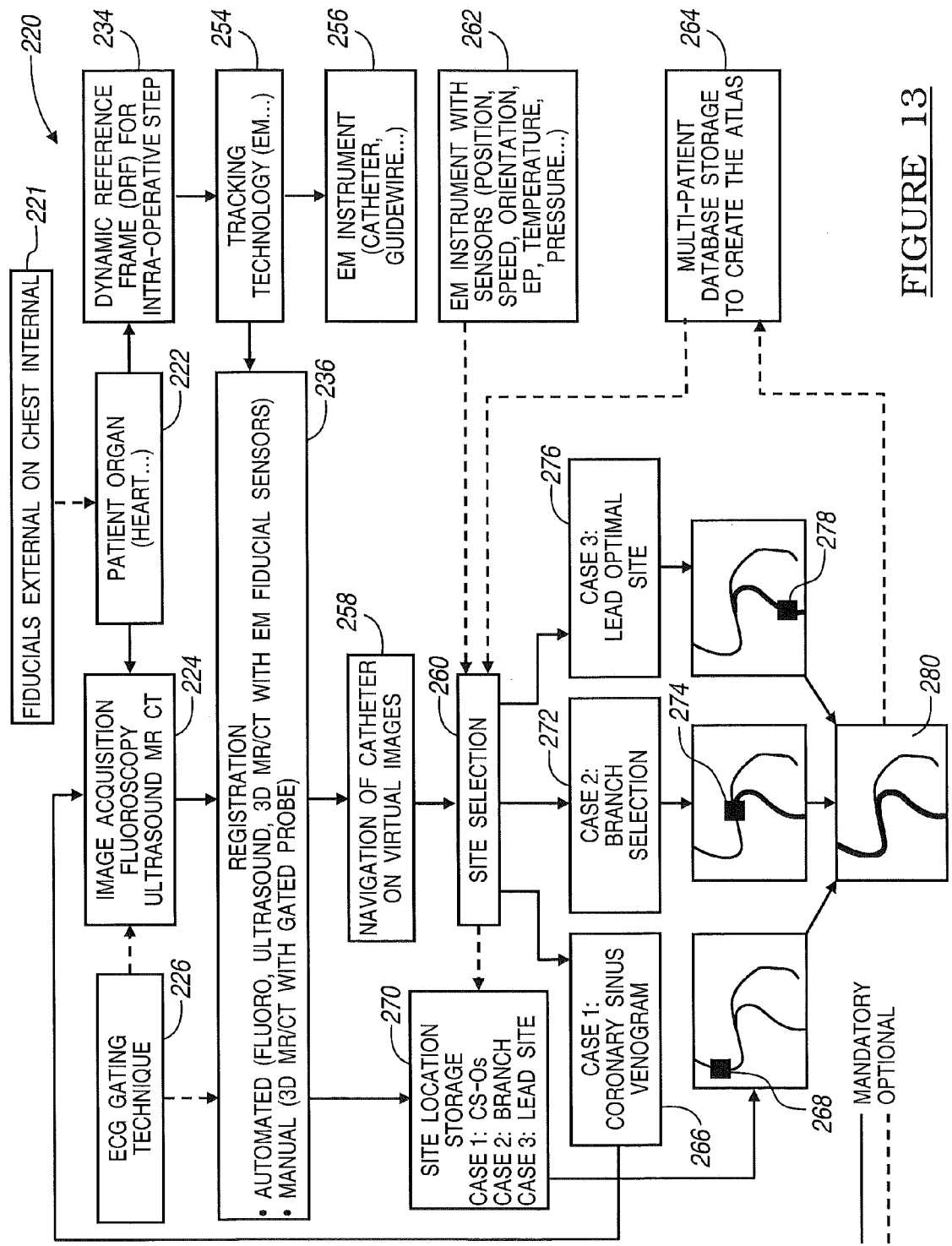
FIG. 13 is a logic block diagram illustrating in further detail a method for navigating the coronary sinus region of the heart.

Turning now to FIG. 13, another exemplary method 220 for navigating a pacemaker lead placement in the heart using a catheter 52 or other instrument is illustrated. The method or procedure 220 is directed to performing image guided coronary sinus cannulation or any other procedure using the navigation catheter 52 or any other instrument in order to position the left heart lead at an optimal site. The navigation system 10 employs the navigation catheter 52 or any other instrument, such as insert or guide wire that carries one or more of the localization sensors 58, to provide information to the user, via display 36. The method 220 begins at block 222 where the particular organ or region of interest is identified. Any organ or soft tissue or region of the patient may be navigated using this disclosed method or procedure. As an exemplary procedure, the coronary sinus region of the heart will be described in further detail.

Once the organ or the heart has been identified, external or internal fiducial markers 60 may be placed on the heart at block 221. Alternatively, any type of anatomical landmark may also be used as the fiducial marker. Still further, contours or paths within the navigated organ may also be used as fiducial markers for the registration process. The procedure then proceeds to block 224 where image acquisition on this region of the patient is conducted. Again, the image acquisition can be from any type of imaging device and can be performed pre-operatively or intra-operatively using a fluoroscope 12, shown in FIG. 1 or any other imaging devices, such as an ultrasound, MRI, CT, etc. The image acquisition process 224 may also be gated, via block 226 to a particular anatomical function. For example, ECG gating using the ECG 62 device may be utilized during the image acquisition 224 to insure that the image is captured or image data is used at a particular sequencing point, via ECG gating 226. In other words, the image may be captured at a particular point or time in a cycle or alternatively if real-time image data is captured over time, image data at a particular point along the time frame may be used, via ECG gating 226. By providing ECG gating 226, the navigation system 10 is able to track the instrument or catheter 52 that is synchronized with the pre-acquired images. In other words, this enables synchronization of the pre-acquired image with the instrument during navigation so that the virtual representation of the instrument or catheter 52 is aligned with the pre-acquired image.

Again, it should be noted that image acquisition process 224 may be gated at block 226 to capture a specific image at a specific time or alternatively, the image data can be a streaming image data continuously captured and the gating 226 may be used to capture image data at a specific time or frame of the already captured image data in order to track the catheter 52. The ECG gating technique 226 also may include gating from any other physiological activity, which is directly or indirectly sensed, via the catheter 52 or other external sensors not associated with the catheter 52. Other types of physiological parameters or activities that can be sensed or used during gating block 226 include blood flow, electrophysiological, respiratory, cardiac, oxygen sensing, $CO_2$ sensing, etc.

Figure 14A:
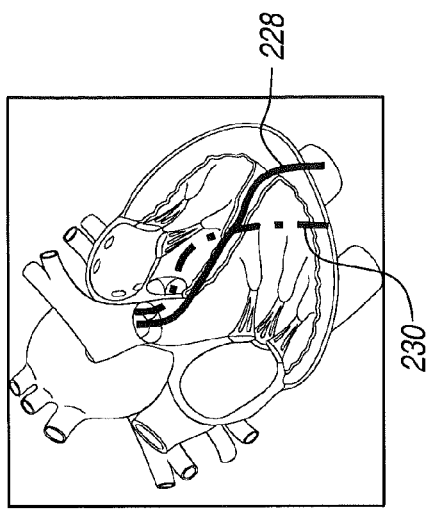
FIGS. 14a and 14b are images of an ungated and a gated tracked catheter.
Figure 14B:
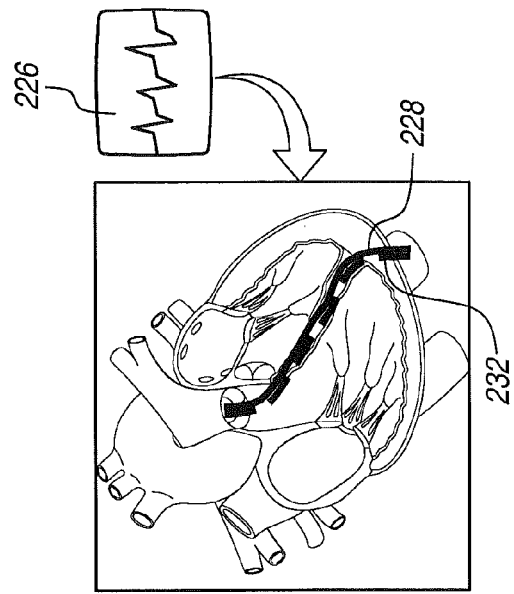

Any soft tissue navigation can benefit from gating or synchronizing to an anatomical function, such as the heartbeat, respiratory, etc., as previously discussed. For example, referring to FIGS. 14a and 14b, a pre-acquired fluoroscopic image of the heart is illustrated with a virtual representation of the catheter 52. As shown in FIG. 14a, the fluoroscopic image of the heart acquired with a real catheter is identified as reference numeral 228. The virtual representation of the navigating catheter 52, is shown as reference numeral 230. The superimposed catheter 230 does not match catheter 228 because it is not synched with the originally captured image 228. In other words, when the pre-acquired image 228 was captured, it was arbitrarily captured and not gated to a specific physiological event. Therefore, when the superimposed catheter 230 was localized to the pre-acquired images, it resulted in a mismatched or unsynched image. In contrast, referring to FIG. 14b, using the ECG gating technique 226, since the navigation system 10 knows when the image 228 had been acquired in the particular heartbeat cycle, it is possible to sync the superimposed or virtual representation of the instrument 232 with the image 228 to generate a good match.

Returning to FIG. 13, at block 234, one or multiple dynamic reference frames 54 are affixed to the patient 14, either internally, via a lead or externally, with an adhesive patch on the skin. The dynamic reference frames 54 may also include fiducial markers 60, as previously discussed and used for the registration process.

Images of the navigated organ, such as the heart 222, are acquired at block 224 during the procedure 220. Each of the images acquired at block 224 is registered to the patient at block 236, either manually using fluoroscopy, ultrasound, or other known techniques by using fiducial markers 60 that can be located on the pre-acquired images. Alternatively, if the fiducial markers 60 contain EM position sensors then automatic registration is possible. An exemplary sensor that includes both a dynamic reference frame and a fiducial marker, is set forth in U.S. Pat. No. 6,381,485, entitled "Registration of Human Anatomy Integrated for Electromagnetic Localization", issued Apr. 30, 2002, where is hereby incorporated by reference. In a case of pre-operative or intraoperative imaging, such as cardiac-gated MRI or CT, the registration may also be gated at the same event during the heart cycle to optimize the registration accuracy at block 226.

There are various types of registration procedures to be utilized that can be optionally gated, via the ECG gating 226. Again, patient registration is the process of determining how to correlate the position of the instrument or catheter 52 in the patient 14 to the position on the pre-acquired or intra-operative acquired images. There are typically four different ways of registering the position of the catheter 52 in relation to the images acquired at block 224. The first registration procedure is point registration. With point registration, the pre-operative images acquired may be synchronized by the ECG gating block 226. To manually register the patient 14, the physician will select landmarks or particular points identified in the pre-acquired images and then touch the corresponding points in the patient's anatomy with the pointer probe 66. By selecting the internal or external landmarks on the anatomy or fiducial markers 60 that are identifiable in the pre-acquired images, it is possible to establish a relationship with the coordinate system for navigation. To perform an automated point registration process, the fiducial markers 60 may also include the dynamic reference frames 54.

The second type of registration is a surface registration technique. This technique is substantially similar to the point registration technique, except that the pointer probe 66 or the catheter 52 is dragged or passed along the patient's anatomy, either internally or externally. By using surface recognition software, as is known in the art, the navigated surface can be automatically matched with the corresponding surface in the pre-acquired image. Again, to increase accuracy further, this registration technique may also be synched to when the pre-acquired image was captured, via block 226.

Another technique for registering two different modalities is by a path registration technique using the EM catheter 52. When the EM catheter 52 penetrates a specific region in the anatomy, such as a vein, it is possible to store the location of the sensors 58, along the path by collecting the sensor data in synchronization with the heartbeat time (ECG gating 226). A virtual 3-dimensional curve can then be built to represent an actual cavity or vessel. Using known pattern recognition or distance map algorithms, it is then possible to locate and find the specific shape of that curve in the pre-operative scan or image and get an automatic path registration.

Figure 15C:
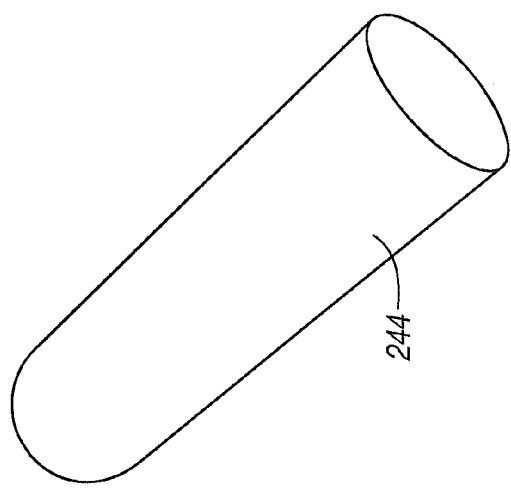
FIGS. 15a-15c illustrate a navigable catheter employed in cardiac therapies, according to the teachings of the present invention.
Figure 15B:
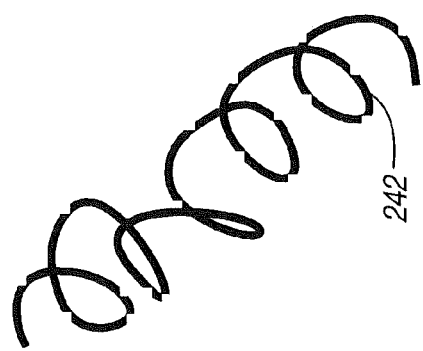
Figure 15A:
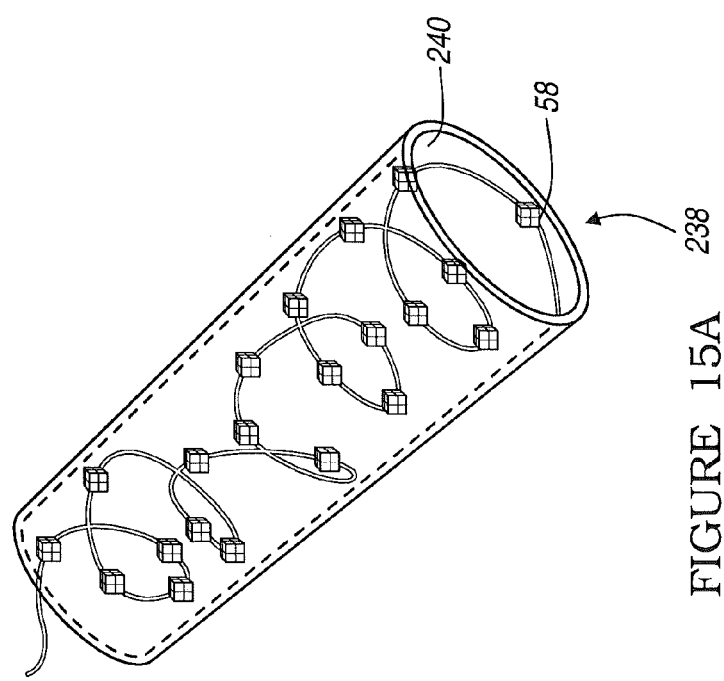

Examples of types of catheters used for the path type registration technique include spiral or balloon catheters, as illustrated in FIGS. 15a-15c and 16, respectively. As shown in FIG. 15a, a spiral catheter 238 is illustrated that includes electromagnetic coil sensors 58 positioned spirally within the inner surface of the vein 240. The advantage of the spiral catheter, is that there is no blood obstruction within the vein 240 and no risk of balloon deflation issues. FIG. 15b illustrates the data collection and virtual 3D curve 242 that is constructed from the sensed signals, via spirally oriented sensors 58. The virtual 3-dimensional curve 244 is illustrated in FIG. 15c, which represents the final 3D shaped vessel, based on the curve 242, which represents the vein that is to be matched with a segment vein in the pre-operative or intraoperative scan.

Turning to FIG. 16, a balloon catheter 246 that includes a plurality of balloons 248, each having sensor coils 58 located therein, is illustrated. Here again, the balloons 248 fit in the vein 250 and center the coils 58 to match the 3-dimensional shape of the vein 250. Here again, this enables a final 3D shape of the vein 250 to be modeled and matched with a segmented vein in the pre-operative scan or intraoperative scan.

Another type of registration process, as previously discussed, involves the 2D/3D registration of a fluoroscopic image and a pre-op scan, which are each synchronized using the ECG gating technique 226. With both modality images acquired at the same time during a heartbeat, both images are then static and potentially matchable. This non-invasive method merges the 3D pre-operative scan with the 2D image. One way to automatically register the heart with fluoroscopy and CT or other imaging modality is to use the spinal vertebrae that is next to the heart itself as the anatomical landmark. The thoracic vertebrae are key landmarks to get the automatic 2D to 3D registration. In the alternative, angiography and the use of vessels themselves for registration between both modalities may also be utilized. Alternatively, known 3D to 3D or 4D to 4D registration may also be employed.

Returning to FIG. 13, once the image acquired during the image acquisition phase 224 has been registered to the patient at block 236 using ECG gating techniques 226, the procedure proceeds to block 254 where the instrument or catheter 52 is tracked using the navigation system 10. Again, the navigation system 10 utilizes the electromagnetic tracking system 44 or any other type of tracking system, such as optical, acoustic, conductive, etc. From the tracking block 254, the process 220 includes block 256 that identifies the electromagnetic instrument, such as the catheter 52 or guide wire that is being tracked in the tracking block 254. Again, the instrument 52 may either receive or transmit electromagnetic signals enabling the tracking system 44 to identify the location of the instrument 52 relative to the patient 14 and relative to the pre-acquired images during the image acquisition block 224, via the registration block 236. This enables navigation of the catheter 52 or any other instrument relative to the pre-acquired images at block 258. Again, once the images from block 224 have been registered at block 236 and synchronization, via ECG gated block 226, the navigation catheter 52 is inserted into one of the patient's organs, such as the heart, via block 222 and its virtual representation is displayed on the images, via block 258.

Upon navigating the catheter 52, via block 258, the procedure 220 proceeds to block 260 where the procedure to find an optimized lead placement site is conducted. As an input to this site selection procedure 260, additional sensors may be embedded in the catheter 52, in order to provide cardiac or anatomic function measurements, via internal sensors at block 262. These additional sensors may include an electrophysiological (EP) tip, pressure sensors, temperature sensors, accelerometers, Doppler transducers, tissue sensors, spectroscopy sensors and tracking sensors 58. By using the real-time data received from these sensors in association with the navigation images, the navigation system 10 assists the physician to identify key landmarks or estimated optimized sites on the images 224, such as the coronary sinus. The landmark selection may be manual or automatic by collecting and storing the information of the points on the image 224. Additionally or alternatively, the navigation system 10 may display one or more multiple color coded maps, via display 36, based on the data each sensor communicates to the navigation system 10. For example, temperature maps can be overlaid in real-time on the images 224, based on the temperature, the catheter 52 temperature sensor transmits. Also, the EP signal can be assigned to the collective points to assist the physician to make a decision where the coronary sinus is or is not.

Further information that can be delivered at block 262 includes a catheter or instrument information. In this regard, various catheters or instruments have flexibility or bending parameters, which enables different types of catheters to be navigated to different types of sites. This is sometimes referred to as a tortuocity factor. Navigating through a tortuous vascular structure generally requires a catheter to be very flexible and bendable without fracturing or failure. This type of information may also be delivered, via block 262 to insure that the proper catheter is being utilized to be navigated in the appropriate site. If it is determined that the site is too tortuous for the particular catheter utilized, the system will identify this to enable the surgeon to select a more appropriate catheter or instrument, via the tortuocity factor.

Multiple EM catheters 52 may also be utilized and positioned on the left and right side of the heart to track the motion of the left and right side of the heart in order to optimize the heart function and pacing performance. In this regard, both sides of the heart are tracked to insure that they are balanced in order to have the proper flow, thereby optimizing the lead placement based on knowing this balance.

Moreover, if the image acquisition 224 is based on an ultrasound image, or if the catheter includes an internal ultrasound transducer sensor then Doppler information is available to provide hemo-dynamic data relative to the position. In this regard, the hemo-dynamic information enables a physician to calculate ejection fractions in the cardiac area to determine the volume of blood and flow through the heart using the Doppler technique. By measuring the volume of blood moving in and out of the chambers, this also provides further cardiac or physiological measurements in order to optimize the lead placement, via the information provided at block 262. In other words, by using a dynamic 3D ultrasound imaging modality or a Doppler sensor in the catheter 52, this enables a physician to visualize the anatomy in space over time. This spatio-temporal Doppler technique is useful for the hemo-dynamic studies and enables calculation of the ejection fraction in the cardiac area. By combining both anatomy information, hemo-dynamics from real-time spatio-temporal echography, localization and navigation technology to select an optimum lead placement at block 260, it is possible to significantly improve pacing performance and thus, patient outcome.

Thus, site selection at block 260 for the lead placement is optimized by providing an estimated optional site based on real-time anatomic or physiological information, navigation or localization information, hemo-dynamic data, and electrophysiological data, as opposed to simply stuffing the lead into the heart without any optimization. By improving the pacing performance of the therapy, the muscle is paced in its more normal function and overall heart function is improved. In contrast, if lead placement is not optimized, the heart may not function properly, thereby degrading other areas or muscles in the heart as they try to compensate for non-optimized performance.

An additional input to the site selection block 260 is a multi-patient database storage or atlas 264 that provides previously acquired patient information or an atlas template on the estimated lead placement site. This atlas can be created by recording information used during the lead placement procedure, based on the anatomy and functional data at block 262. This atlas template at block 264 may provide an estimated target that can be visualized on the display 36 as the catheter 52 is navigated during the site selection process 260. Also during the current procedure, this information is stored and recorded at block 264 to update and improve the atlas template. In other words, as you are collecting all of this information during the procedure 220, an atlas is created at block 264, which can then determine and give estimates of what the most likely and best place for lead placement is. The ultimate outcome is trying to locate the best location for lead placement in order to provide the best performance for the heart. For example, assuming that one hundred previous procedures on one hundred patients have been performed and the information was recorded during these procedures that identified the path and sites where the leads were placed for optimized performance, for the one hundred and first procedure, the physician will use the previously acquired one hundred procedures to further optimize the results. This will provide a path to guide the physician to an estimated optimized site, which can be accessed via the site selection process at block 260.

Based on the multiple maps (position EP, speed, temperature, hemo-dynamic, etc), the physician can identify the coronary sinus osteum and cannulate the coronary sinus. In this regard, at block 266, the catheter 52 is guided to an estimated initial site location 268, via the site location storage block 270 that stores the estimated sites using information from blocks 262 and 264. Once in the coronary sinus, a contrast agent may be administered through the navigation catheter 52. Images of the coronary sinus can be acquired to create a new road map for lead placement. Again, these images can be gated or not, and acquired in 2D, 3D or 4D. Once the revised or updated road map is established and registered at block 236, the instrument, such as the catheter 52 or guide wire is used to select the branch for lead placement, via block 272 and target or site 274. During this procedure, the catheter 52 is pushed and visualized a real-time using images acquired during the contrast agent use. Again, in the coronary sinus osteum to the end lead placement site, this path is stored with the patient database 264 and will be displayed as an overlay on the image for future reference.

Once the branch 274 has been selected, via navigation system 10, an optimal site for the lead is selected at block 276 identified by estimated target or site 278. By tracking the catheter displacement with the position sensors 58 and by pacing the left heart, it is again possible to optimize the function of the heart. Also, with additional right heart catheter sensors, the overall cardiac function can be optimized, based on accelerometry gathered from the position sensors on both sides of the heart and by real-time measuring of the cardiac wall motion, thereby optimizing the lead site 278. Also, by using the other sensors or other imaging modalities, such as the ultrasound or Doppler, via either an ultrasound imaging device or Doppler sensor in the catheter 52, hemo-dynamic information is gathered. This information is also used to provide an optimized lead site 278. This optimized site 278 may be estimated and identified, via the target 278 or selected by the physician upon reviewing all of the information, via blocks 262 and 264.

Once the optimal site 278 of the lead placement has been selected, the location and path is stored in a computer and displayed on image 280. The lead can then be placed over the guide wire or through the catheter 52 and directed to the desired optimized site 278. A final check on the performance is evaluated before the procedure 220 is ended. In the event of a failure, lead dislodgement or other cause, the stored path 280 that has been acquired during the implantation procedure can be reused as a road map for the new lead placement. This can also be used and overlaid on future pre-acquired images as a 3D surgical road map for future patients.

Other uses of the procedure 220 may include an electromagnetic guided biopsy catheter 282, illustrated in FIGS. 17a and 17b. In this regard, every heart transplant patient undergoes an annual check-up to measure for early indicators of organ rejection in order to determine and confirm that the heart is still not rejected by the patient's body. These indicators include white blood cells, chemical charges, blood oxygen labels, etc. To make this determination, an endovascular biopsy catheter is inserted into the heart and multiple biopsies are performed in the septum wall of the heart between the left and right side of the heart. In conventional tests, a fluoroscopic procedure is performed utilizing contrast agent and continuous fluoroscopic images are used to select approximately ten biopsy samples in the septum. Again, this leads to exposing the patient to radiation and contrast agents, which is undesirable. By providing an EM guided biopsy catheter 282, the procedure can be optimized and radiation and contrast agent use can be reduced or eliminated all together following the procedure similar to that disclosed in procedure 220.

The catheter 282 is similar to a standard endovascular biopsy catheter that includes a flexible shaft 284 having a distal biopsy end 286 with a plurality of biopsy graspers 288 to engage and capture a biopsy sample. Located at the proximal end of the catheter 282 is a fixed handle 290 and a movable portion 292, which articulates the graspers 288. Located within the shaft 284 are a plurality of electromagnetic sensors 294 that operate similar to the sensors 58 in the catheter 52. In this way, the shaft and the distal end of the catheter 282 may be tracked via the electromagnetic tracking system 44.

By utilizing the techniques set forth in the procedure 220, shown in FIG. 13, along with the electromagnetic guided biopsy catheter 282, the distal end of the catheter 282 may be precisely guided to optimum sample sites in the septum without the constant radiation exposure and reduced or eliminated use of contrast agents. Moreover, by again building a database to create an atlas map, various optimized sample site locations can be identified in the pre-acquired images, so that the catheter 282 can simply be navigated to these sample sites to gather the biopsy tissue. Thus, only a couple of images are required to perform this task instead of using constant radiation to visualize the biopsy catheter and a more precise sampling can be achieved. It should further be noted that the biopsy catheter 282 may be utilized to biopsy other areas of the patient as well, such as the spine, cervical or other regions of a patient 14.

The procedure 220 may also be used for a catheter-based approach using the navigation system 10 to treat neurological disease. In this regard, today most of the neurological diseases are treated and accessed from the cranium down to the neurological site in order to treat diseases, such as tumors, ventricle blockages, Parkinson's, aneurysm, etc. However, this type of treatment results in significant trauma due to forming a skull hole, dura opening, fiber destruction, or other cerebral structural damage. Also, cell, drug, or gene delivery generally cannot be taken orally because the product delivered is destroyed by the digestive system. Therefore, site specific delivery is needed. A minimally invasive navigation approach is possible since all cerebral structures are accessible from either vascular or cerebrospinal fluid tree (CSF) access. By using the catheter 52 equipped with the EM sensors 58 that can be tracked by the EM tracking system 44 and by using the image registration techniques 236 to overlay the position of the catheter 52 onto a pre-operative (CT, MRI, etc.) and or intra-operative (fluoroscopy, ultrasound, etc) images, the catheter 52 may be steered from the jugular, groin, or spine all the way to the neurological site, via the endovascular or the cerebral fluid tree path. At the neurological site, treatment can then be delivered and provided.

For example, site specific therapy can be delivered, such as gene, drug, or cell delivery at the site specific area. For aneurysm treatment, a site specific biologic or embolic treatment can be delivered to attempt to correct the aneurysm. With Parkinson's disease, lead placement through the third and fourth ventricle using the cerebral fluid tree is possible. At the caudate nucleus, a biological patch delivery using the cerebral fluid tree is also possible. The procedure may also be used for shunt placement to correct an occlusion. Here again, instead of drilling a hole, a minimally invasive approach through either the endovascular or cerebrospinal tree is an option. Again, these types of neurological procedures may also be optimized by sensing various surrounding anatomical functions with the catheter 52 or other instrument to again optimize lead placement or optimize gene, cell or drug delivery by providing an estimated delivery site.

Figure 18A:
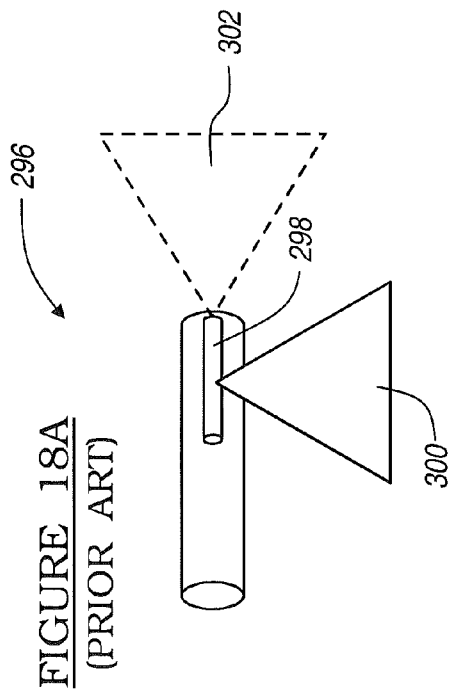
FIGS. 18a and 18b illustrate a prior art intravascular ultrasound (IVUS) catheter.
Figure 18B:
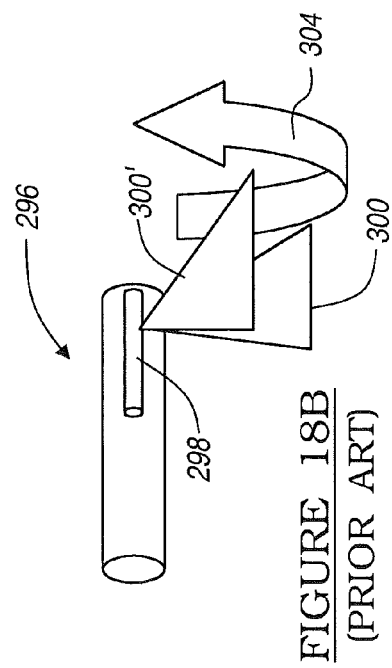

Turning now to FIGS. 18a and 18b, a prior art intravascular ultrasound (IVUS) catheter 296 is illustrated. The IVUS catheter 296 is a disposable catheter that includes an ultrasound transducer 298 that is typically used to visualize tissue and/or blood vessels in a minimally invasive approach. The IVUS catheter 296 is a disposable catheter that is also very costly. The transducer 298 enables visualization only from a side view plane 300 and does not provide a forward view 302 whatsoever. The single side view 300 is available with the catheter 296 positioned statically. Should the IVUS catheter 296 be rotated about arc 304, as illustrated in FIG. 18b, various side view planes 300, 300', . . . are available about the rotation axis 304.

Figure 19:
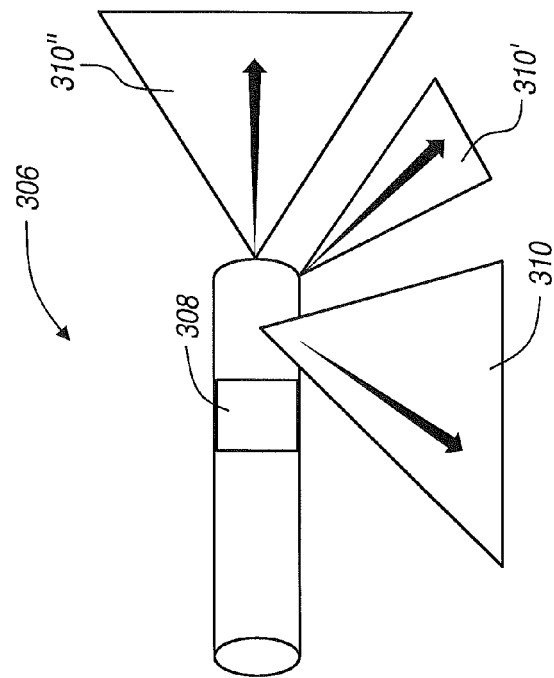
FIG. 19 illustrates a virtual intravascular ultrasound catheter, according to the teachings of the present invention.

Referring now to FIG. 19, a virtual intravascular ultrasound (IVUS) catheter 306 according to the teachings of the present invention is illustrated. The virtual IVUS catheter 306 includes at least one electromagnetic tracking sensor 308 or multiple tracking sensors positioned along its shaft to again track the location of the virtual IVUS catheter 306 with the electromagnetic tracking system 44. Again, it should be noted that any other type of tracking system and sensors may also be utilized. The virtual IVUS catheter 306 is able to generate virtual IVUS views from an infinite number of planes or direction 310, 310', 310" from any angle or position relative to the catheter 306, further discussed herein.

Figure 20:
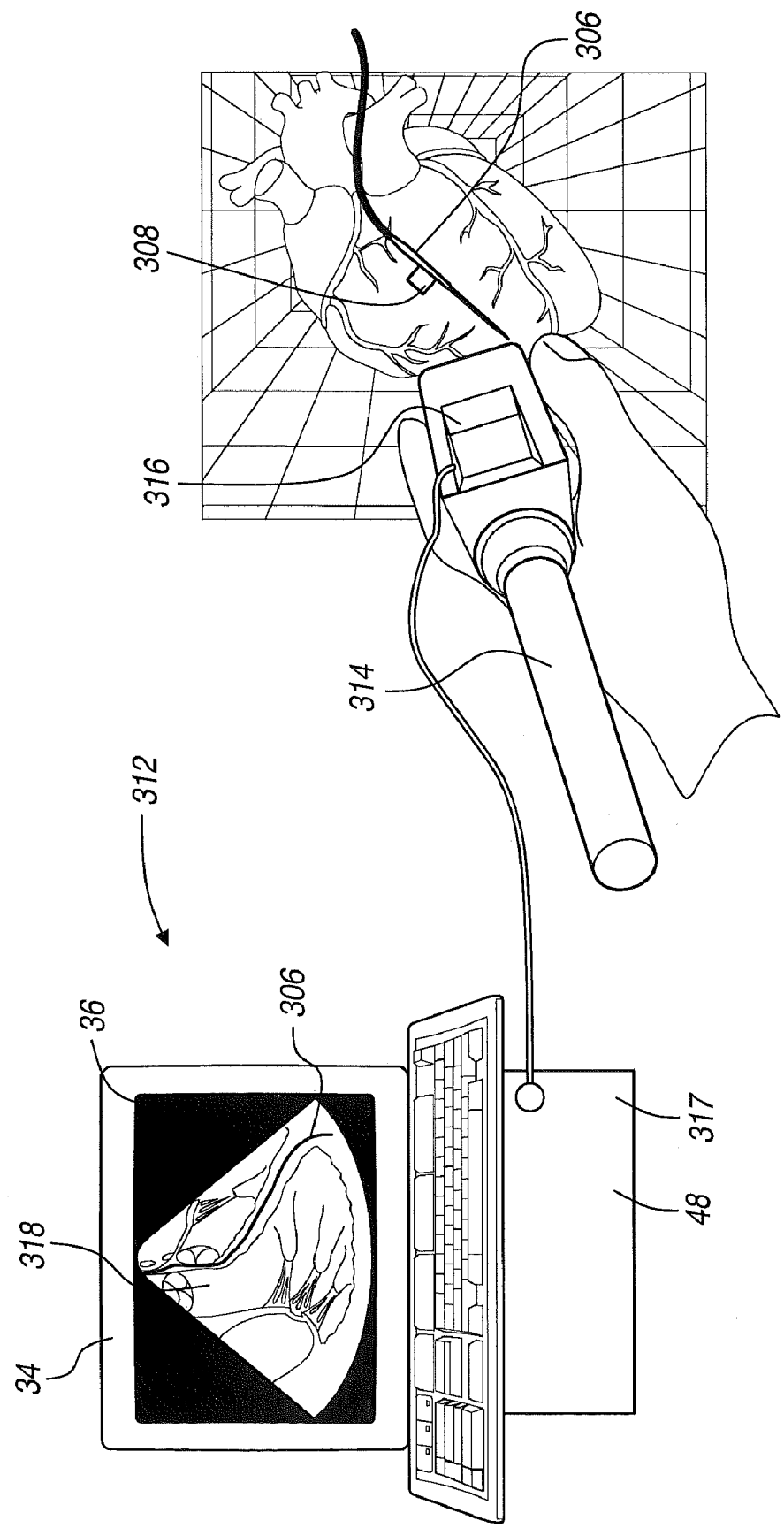
FIG. 20 illustrates a virtual intravascular ultrasound system, according to the teachings of the present invention.

Referring to FIG. 20, a virtual IVUS system 312 according to the teachings of the present invention is illustrated, which includes the virtual IVUS catheter 306 having the sensor 308. The virtual IVUS system 312 works in combination with the navigation system 10 and employs the electromagnetic tracking system 44. With this type of configuration, an ultrasound imaging modality may be used to replace the fluoroscopic imaging device 12 or the imaging device 12 may be used in combination with the ultrasound imaging modality. In this regard, a dynamic 3D ultrasound probe 314, such as the Phillips XMatrix probe, combined with an electromagnetic tracking sensor 316 is positioned outside the body of the patient 14 and connected to an ultrasound controller 317. The ultrasound controller 317 may be a separate controller or combined with the work station 34 and coil array controller 48. By using the 3D probe 314 with the electromagnetic sensor 316, the field of view of the probe 314 is calibrated to the EM coordinate system of the electromagnetic tracking system 44. By tracking the flexible EM catheter 306 equipped with at least one electromagnetic sensor 308, the controller 317 can generate a virtual IVUS view from that coil position, as illustrated in FIG. 19. In other words, the dynamic 3D ultrasound imaging modality from the 3D ultrasound probe 314 allows a physician to visualize the anatomy in space over time. By tracking the flexible catheter 306 equipped with at least three EM coils 308, it is possible to superimpose the catheter 306 onto this spatio-temporal echographic image. The three coils of the catheter 306 represent the planes in the space over time from the perspective of the catheter 306. The equation of those planes may then be calculated to display the corresponding echographic spatio-temporal plane to visualize the catheter 306 in its entire shape in a real-time echographic image or from the point of view of the catheter.

Therefore, by providing a very cost effective catheter 306 that does not include an ultrasound transducer in the catheter, but uses the external ultrasound probe 314, virtual IVUS images can be produced and displayed at any angle or direction relative to the catheter 306 or from the catheter's point of view. This enables the physician to superimpose the catheter 306 onto the image 318, illustrated on display 36, as well as generate a field of views from the forward position of the catheter 306. The system also operates to either take a slice of the 3D ultrasound relative to its current location or it may also identify and generate a view of its total path that the catheter or instrument has transversed through. The system 312 also provides a look ahead view as it moves relative to the catheter 306. Basically, the system 312 creates slices based on the vessel position and views transverse to the vessel or axial to the vessel along curved paths or straight paths. Projected trajectories of the forward advance of the catheter 306 can also be tracked and superimposed on the image 318. It should also be noted that while a 3D ultrasound probe 314 has been discussed, a 4D probe or other imaging modalities, such as MRI, CT, OCT and spectroscopy may also be utilized to create the virtual views. Thus, by automatically registering the probe 314 having the sensor 316 relative to the catheter 306 having the sensor 308 using the navigation system 44, automatic registering between these two systems without requiring motion correction is available. Moreover, the ultrasound image, which is registered via the probe 314 and catheter 306, may also be registered or linked with any other image modalities. In this regard, the ultrasound image modalities may be registered relative to fluoroscopic, MRI, CT, or other image modalities and displayed at one time on the display 36 to provide a further level of information.

In addition to providing a three-dimensional image volume, the ultrasonic probe 314 may also provide a three-dimensional Doppler volume by switching the ultrasound probe 314 to the spatio-temporal Doppler format. From this Doppler volume, the physician can visualize a metric or statistical measurements for blood flow or motion at the tip of the catheter 306. Again, this system would then not be visualizing an ultrasound image, but visualizing statistics or measurements. This information can be conveyed using color coded figures that are displayed on the display 36. For example, should the catheter 306 be guided through a blood vessel and the Doppler effect measure the volume of blood flow going through the vessel at a certain point, where there is an occlusion, there would be much smaller blood flow on one side of the occlusion than on the other. The quicker blood flow can be characterized by red on one side of the vessel and blue on the occluded side, thereby identifying where the occlusion is within the vessel. Other anatomical functions may also be sensed as previously discussed, such as pressure, temperature, etc and also visualized on the display 36. This again enables the navigation system 10 to identify an estimate site to navigate to and deliver a therapy (e.g., ablation).

In addition to navigating and visualizing the area of interest, the catheter 306 or other instrument may also deliver therapy at the point of interest. For example, the catheter 306 may delivery a drug, ablate, or deliver a lead or other device following the procedure 220. With drug delivery, a profusion model may be overlaid over the tracked image that models the flow of the drug depending on the dosage and type of drug delivered. This overlay can be color coded to identify the region that the drug will interact at the area of interest. Also, by providing sensors at the catheter 306, real-time monitoring of the drug delivery may also be visualized on the display 36, thereby providing real-time feedback on the diffusion through the tissue of the drug delivery. In this way, proper dosage of the drug delivery is achieved. These templates can also identify therapy effective zones, such as ablation zones in the area that the ablation may affect before the ablation is performed. This also provides an optimized procedure.

With all of the identified procedures, a dual delivery therapy may also be provided. For example, with drug therapy, some drugs require stimulation to activate the drugs, such as by heat, while other drugs may require a second drug to activate. Thus, the instrument or catheter utilized to navigate to the particular optimized site can both deliver the drug and also heat it using a heat probe or deliver a second drug in order to activate it and provide better performance. The drug delivery may also include magnetically conductive components, so that the pattern or direction of where the drug delivery is applied is controlled, via a magnetically sensitive sensor attached to the catheter. The drug delivery or any other type of delivery, such as cell or gene delivery may also be gated or synched to an anatomical physiological function, such as the heartbeat, via the ECG monitor 62 or other devices. In this way, by gating the delivery to the particular cycle, proper placement and dosage of the drug, gene or cell delivery is also optimized.

The instruments may also deliver the drugs, genes or cells using a pattern delivery technique. With this type of technique, drugs may be delivered over a significant area. For example, a 9×9 grid spaced about 0.1 millimeters apart may be the delivery area. The catheter 52 may be provided with multiple delivery needles, such as 3×3 grouping of needles, thereby requiring only nine deliveries to fill the 9×9 area. This again delivers the drug to the needed area, thereby optimizing the result of the drug delivery and reducing the time for delivering the drug. Moreover, the catheter may also include a sensor to provide additional feedback on the delivery to again identify that a sufficient amount of drug has been delivered. In which case, the delivery plan may be able to be changed using this real-time feedback. This delivery plan can again include an icon representing where the drug delivery should take place that is determined by the navigation system 10.

Figure 21:
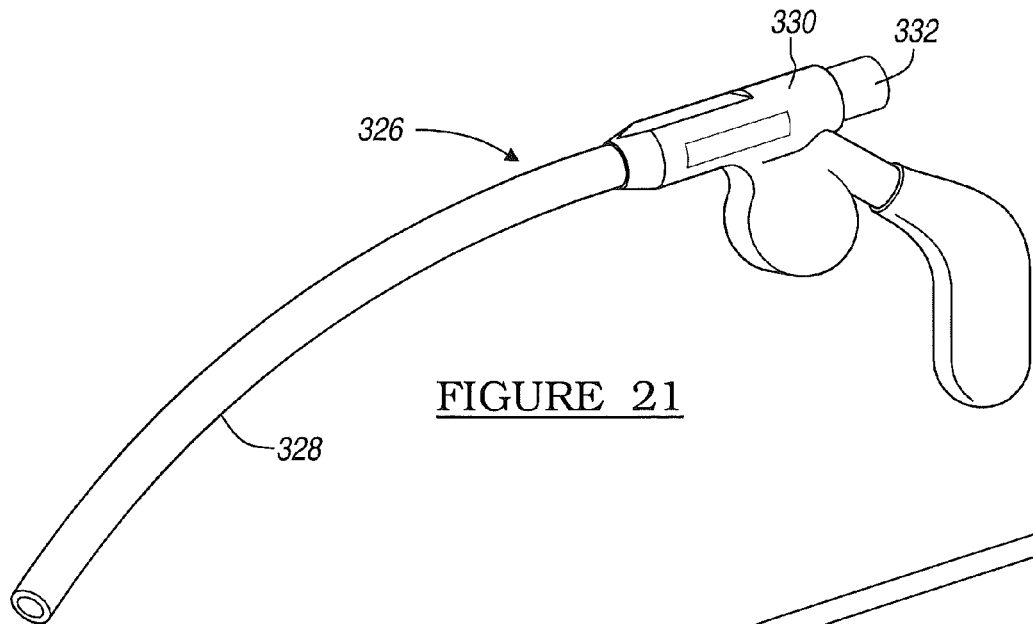
FIG. 21 illustrates an exemplary catheter utilized according to the teachings of the present invention.
Figure 22:
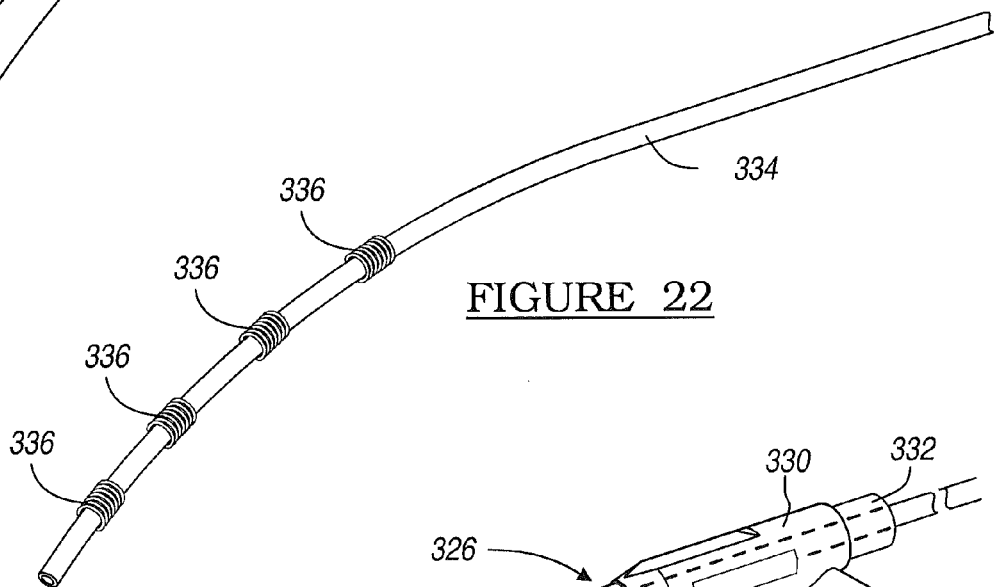
FIG. 22 illustrates an exemplary tracking insert utilized with the catheter of FIG. 21.
Figure 23:
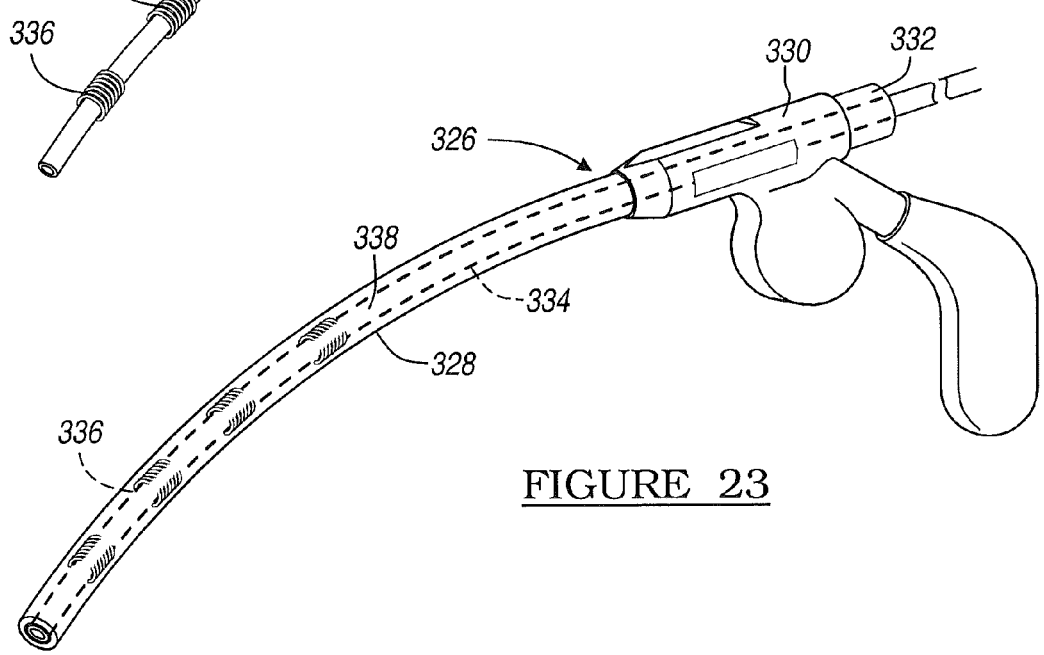
FIG. 23 illustrates the assembly of the insert and catheter of FIGS. 21 and 22 according to the teachings of the present invention.

Referring to FIGS. 21-23, an exemplary catheter, along with a delivery insert, which may be used with the navigation system and procedure disclosed herein is discussed in further detail. As illustrated in FIG. 21, a catheter 326 is illustrated to include a delivery tube 328 and a handle 330 that defines a passage 332 in communication with the tube 328. As shown in FIG. 22, a multi-sensor insert 334 is illustrated that includes four sensor coils 336. The insert 334 is electronically in communication with the navigation probe interface 50, similar to the catheter 52 illustrated in FIG. 1. The insert 334 is operable to be slidably inserted within passage 332 defined in handle 330 in order to pass into delivery tube 328, as illustrated in FIG. 23. The insert 334 enables the use of various conventional catheters, such as the catheter 326 without requiring further modification to existing catheters. In other words, use of the insert 334, having electromagnetic sensors 336 enables conventional catheters to be converted to a navigable tracked catheter by simply passing the insert 334 within the catheter 326. The insert 334 includes a cannula 338 to enable delivery of various therapies through the catheter 326 and insert 334 once the insert 334 has been navigated to the appropriate site, via the catheter 326. For example, a lead may be passed through the cannulation of the instrument 334 during a cardiac lead placement, as previously discussed.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An image guided navigation system for guiding an instrument through a region of a patient, said image guided navigation system comprising:
    a tracking device operable to track the position of the instrument in the region of the patient;
    a controller operable to receive anatomical gating information regarding a physiological event and receive captured image data of the region of the patient in response to said physiological event, and in communication with said tracking device and operable to automatically register said image data with the region of the patient at least with said physiological event by,
        collecting a position of the instrument as the instrument moves through at least a portion of the region of the patient synchronized with said physiological event,
        building a virtual three-dimensional (3D) curve of at least the portion of the region of the patient, and
        comparing the built virtual 3D curve with a shape of an anatomical curve in the captured image data; and
    a display operable to display the captured image data of the region of the patient with a superimposed icon representing the instrument, wherein said controller is further operable to superimpose the icon representing the instrument onto the image data of the region of the patient based upon the position tracked by said tracking device;
    wherein comparing the built virtual 3D curve with the shape of the anatomical curve in the captured image data includes executing instructions with the controller including at least one of pattern recognition algorithms or distance map algorithms to locate and find the specific shape of the built virtual 3D curve with an identified shape of the anatomical curve in the captured image data.

2. The system of claim 1, wherein at least the portion of the region of the patient is a vessel in a vasculature of the patient.

3. The system of claim 2, wherein the instrument is operable to pass through the vasculature of the patient to a heart of that patient.

4. An image guided navigation system for guiding an instrument through a region of a patient, said image guided navigation system comprising:
    a tracking device operable to track the position of the instrument in the region of the patient;
    a controller operable to receive anatomical gating information regarding a physiological event and receive captured image data of the region of the patient in response to said physiological event, and in communication with said tracking device and operable to automatically register said image data with the region of the patient at least with said physiological event by,
        collecting a position of the instrument as the instrument moves through at least a portion of the region of the patient synchronized with said physiological event,
        building a virtual three-dimensional (3D) curve of at least the portion of the region of the patient, and
        comparing the built virtual 3D curve with a shape of an anatomical curve in the captured image data; and
    a display operable to display the captured image data of the region of the patient with a superimposed icon representing the instrument, wherein said controller is further operable to superimpose the icon representing the instrument onto the image data of the region of the patient based upon the position tracked by said tracking device;
    wherein the tracking device includes a plurality of tracking devices;
    wherein the instrument includes a spiral catheter including the plurality of the tracking sensors positioned apart along a length of the spiral catheter, wherein the spiral catheter is operable to be positioned spirally within the inner surface of the at least a portion of the region of the patient, wherein a position of each of the plurality of tracking devices is operable to be determined by the controller to build the virtual 3D curve.

5. The system of claim 4, further comprising:
    a dynamic reference frame operable to be connected to the region of the patient, wherein the dynamic reference frame includes a frame tracking device and is operable to be tracked to maintain registration;
    wherein a right side of the heart and a left side of the heart are tracked simultaneously to assist in optimizing lead placement.

6. An image guided navigation system for guiding an instrument through a region of a patient, said image guided navigation system comprising:
    a tracking device operable to track the position of the instrument in the region of the patient;
    a controller operable to receive anatomical gating information regarding a physiological event and receive captured image data of the region of the patient in response to said physiological event, and in communication with said tracking device and operable to automatically register said image data with the region of the patient at least with said physiological event by,
        collecting a position of the instrument as the instrument moves through at least a portion of the region of the patient synchronized with said physiological event,
        building a virtual three-dimensional (3D) curve of at least the portion of the region of the patient, and
        comparing the built virtual 3D curve with a shape of an anatomical curve in the captured image data; and
    a display operable to display the captured image data of the region of the patient with a superimposed icon representing the instrument, wherein said controller is further operable to superimpose the icon representing the instrument onto the image data of the region of the patient based upon the position tracked by said tracking device;
    wherein the tracking device includes a plurality of tracking devices;
    wherein the instrument includes a balloon catheter that includes a plurality of balloons spaced apart along a length of the catheter with each of the plurality of balloons having at least one of the plurality of tracking devices, wherein the plurality of balloons are configured to fit in the at least the portion of the region of the patient, wherein a position of each of the plurality of tracking devices is operable to be determined by the controller to build the virtual 3D curve.

7. The system of claim 6, wherein each of the tracking devices are substantially in a center of each of the respective balloons.

8. The system of claim 7, wherein the controller is further operable to segment the captured image data to identify the shape of the anatomical curve in the captured image data prior to the comparing the built virtual 3D curve with a shape of a curve in the captured image data.

9. The system of claim 8, further comprising:
a dynamic reference frame operable to be connected to the region of the patient, wherein the dynamic reference frame includes a frame tracking device operable to be tracked to maintain registration;
wherein a right side of the heart and a left side of the heart are tracked simultaneously to assist in optimizing lead placement.

10. An image guided navigation system for guiding an instrument through a region of a patient, said image guided navigation system comprising:
an instrument operable to be positioned within the region of the patient;
a sensor connected to the instrument and operable to be positioned with the instrument within the region of the patient and generate a signal based on a sensed feature in the region of the patient;
a tracking device operable to track a position of the instrument in the region of the patient;
a controller operable to receive anatomical gating information regarding a physiological event and receive captured image data of the region of the patient in response to said physiological event, and in communication with said tracking device and operable to automatically register said image data with the region of the patient at least with said physiological event; and
a display operable to display the image data of the region of the patient with a superimposed icon representing the instrument, wherein said controller is further operable to superimpose the icon representing the instrument onto the image data of the region of the patient based upon the position tracked by said tracking device;
wherein the controller is operable to:
receive the signal from the sensor to find an optimized lead placement site within the region of the patient,
generate multiple color coded maps based on the signal the sensor communicates to the controller, and
execute instructions to automatically register said image data with the region of the patient at least with said physiological event, including:
collecting the position of the instrument as the instrument moves through at least a portion the region of the patient synchronized with said physiological event;
building a virtual three-dimensional (3D) curve of at least the portion of the region of the patient; and
comparing the built virtual 3D curve with a shape of an anatomical curve in the captured image data;
wherein the display is operable to overlay the color maps on the captured image data.

11. The system of claim 10, wherein the sensor includes at least one of a pressure sensor, a temperature sensor, an accelerometer, a Doppler transducer, a tissue sensor, and a spectroscopy sensor.

12. The system of claim 11, wherein the sensor can include a plurality of sensors and further include an electrophysiological (EP) sensor;
wherein each of the plurality of sensors can generate the signal to be received by the controller.

13. The system of claim 11, wherein the signal is operable to be real time with the tracked position of the instrument using the tracking device.

14. The system of claim 11, wherein the color coded maps can include at least one of a temperature map overlaid in real-time on the captured image data based on the signal from the temperature sensor or the signal from an EP sensor can be assigned to a collection of points overlaid on the captured image data.

15. The system of claim 10, further comprising:
an anatomical gating device operable to sense said physiological event; and
an imaging device operable to capture said image data of the region of the patient in response to said physiological event.

16. A method for guiding an instrument through a region of a patient with an image guided navigation system comprising:
receiving information regarding a physiological event with an anatomical gating device;
receiving captured image data of the region of the patient with an imaging device;
tracking a position of an instrument with a tracking device, wherein the instrument and the tracking device are operable to be positioned within the region of the patient;
automatically registering, by executing instructions with a controller, the received captured image data of the region of the patient at least with said information regarding said physiological event, said received captured image data, and said tracked position of said tracking device;
displaying the image data of the region of the patient;
superimposing an icon representing the instrument on the displayed image data;
automatically determining a lead placement site for placement of a lead relative to a heart;
segmenting the captured image data to identify a shape of an anatomical curve in the captured image data; and
comparing a built virtual three-dimensional (3D) curve with the identified shape of the anatomical curve in the captured image data, wherein the built virtual 3D curve is compared to the segmented captured image data;
wherein said superimposed icon represents a position of the instrument relative to the region of the patient based on the registered image data and the position of the instrument tracked by said tracking device.

17. The method of claim 16, wherein capturing the image data is in response to said physiological event sensed with the anatomical gating device;
wherein the automatically registering the image data to the region of the patient is at least with said sensed physiological event.

18. The method of claim 17, wherein automatically registering the captured image data with the region of the patient further includes:
collecting a position of the instrument as the instrument is moved synchronized with said physiological event, and building the virtual three-dimensional (3D) curve of at least the portion of the region of the patient.

19. The method of claim 18, further comprising:
sensing a feature in the region of the patient; and
generating a signal based on the sensed feature in the region of the patient.

20. The method of claim 19, further comprising:
receiving the generated signal with the controller; and
wherein automatically determining a lead placement site for placement of a lead relative to a heart includes executing instructions with the controller to find an optimized lead placement site within the region of the patient.

21. The method of claim 19, further comprising:
positioning a first tracking device in a left portion of the region of the patient;
positioning a second tracking device in a right portion of the region of the patient; and
tracking both the first tracking device and the second tracking device to automatically determine the lead placement site for placement of the lead relative to the heart.

22. The method of claim 19, further comprising:
receiving the generated signal with the controller;
moving the instrument to a coronary sinus;
administering a contrast agent through the instrument;
collecting additional image data of the coronary sinus after administering the contrast agent;
generating a road map for lead placement based on the collected additional image data;
registering the road map to the region of the patient; and
displaying an estimated target site icon superimposed on the registered road map;
wherein the displayed estimated icon is based on the automatically determining a lead placement site for placement of a lead relative to a heart that is based on the generated road map.

* * * * *